United States Patent
Qiu et al.

(10) Patent No.: US 10,729,688 B2
(45) Date of Patent: Aug. 4, 2020

(54) HEPATITIS B ANTIVIRAL AGENTS

(71) Applicant: Enanta Pharmaceuticals, Inc., Watertown, MA (US)

(72) Inventors: Yao-Ling Qiu, Andover, MA (US); Jorden Kass, Arlington, MA (US); Byung-Chul Suh, Lexington, MA (US); Hui Cao, Belmont, MA (US); Wei Li, Lexington, MA (US); Xiaowen Peng, Sudbury, MA (US); Xuri Gao, Newtonville, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 16/365,742

(22) Filed: Mar. 27, 2019

(65) Prior Publication Data
US 2019/0321360 A1    Oct. 24, 2019

Related U.S. Application Data

(60) Provisional application No. 62/649,993, filed on Mar. 29, 2018.

(51) Int. Cl.
| | | |
|---|---|---|
| *A61K 31/4985* | (2006.01) | |
| *C07D 487/04* | (2006.01) | |
| *A61K 31/7105* | (2006.01) | |
| *A61K 45/06* | (2006.01) | |

(52) U.S. Cl.
CPC ...... *A61K 31/4985* (2013.01); *A61K 31/7105* (2013.01); *A61K 45/06* (2013.01); *C07D 487/04* (2013.01)

(58) Field of Classification Search
None
See application file for complete search history.

(56) References Cited

U.S. PATENT DOCUMENTS

| | | |
|---|---|---|
| 3,385,756 A | 5/1968 | Early et al. |
| 3,975,532 A | 8/1976 | Miller et al. |
| 4,285,946 A | 8/1981 | Kampe et al. |
| 4,507,481 A | 3/1985 | Davidson et al. |
| 5,510,387 A | 4/1996 | Leonidov et al. |
| 5,656,644 A | 8/1997 | Adams et al. |
| 6,498,165 B1 | 12/2002 | Armstrong et al. |
| 6,503,913 B1 | 1/2003 | Goldmann et al. |
| 6,525,069 B1 | 2/2003 | Ko et al. |
| 6,667,342 B1 | 12/2003 | Clarke et al. |
| 7,232,825 B2 | 6/2007 | Chen et al. |
| 7,312,214 B2 | 12/2007 | Qiao et al. |
| 7,411,003 B1 | 8/2008 | Liu et al. |
| 7,615,569 B2 | 11/2009 | Fulp et al. |
| 7,741,494 B2 | 6/2010 | Bressi et al. |
| 8,101,643 B2 | 1/2012 | Qiu et al. |
| 8,202,876 B2 | 6/2012 | Albaugh et al. |
| 8,420,823 B2 | 4/2013 | Sato et al. |
| 9,447,086 B2 | 9/2016 | Liu et al. |
| 9,498,479 B2 | 11/2016 | Zhang et al. |
| 9,573,941 B2 | 2/2017 | Liu et al. |
| 9,617,252 B2 | 4/2017 | Liu |
| 9,938,301 B2 | 4/2018 | He et al. |
| 10,179,131 B2 | 1/2019 | Qiu et al. |
| 10,189,846 B2 | 1/2019 | Qiu et al. |
| 10,253,030 B2 | 4/2019 | He et al. |
| 10,428,070 B2 | 10/2019 | Qiu et al. |
| 2002/0068838 A1 | 6/2002 | Demassey et al. |
| 2003/0232842 A1 | 12/2003 | Goldmann et al. |
| 2004/0209930 A1 | 10/2004 | Carboni et al. |
| 2005/0203119 A1 | 9/2005 | Ono et al. |
| 2006/0100233 A1 | 5/2006 | Villa et al. |
| 2007/0219239 A1 | 9/2007 | Mjalli et al. |
| 2007/0225373 A1 | 9/2007 | Chen et al. |
| 2009/0023740 A1 | 1/2009 | Fulp et al. |

(Continued)

FOREIGN PATENT DOCUMENTS

| | | |
|---|---|---|
| CN | 106810548 A | 6/2017 |
| CN | 106928215 A | 7/2017 |

(Continued)

OTHER PUBLICATIONS

Chowdhury. Organic Biomolecular Chemistry, 2011, 9, 5856-5862 (Year: 2011).*

(Continued)

*Primary Examiner* — Noble E Jarrell
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts, esters, or prodrugs thereof:

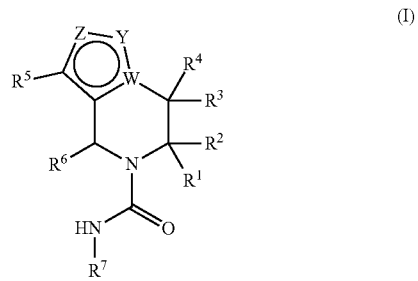

(I)

which inhibit the protein(s) encoded by hepatitis B virus (HBV) or interfere with the function of the HBV life cycle of the hepatitis B virus and are also useful as antiviral agents. The present invention further relates to pharmaceutical compositions comprising the aforementioned compounds for administration to a subject suffering from HBV infection. The invention also relates to methods of treating an HBV infection in a subject by administering a pharmaceutical composition comprising the compounds of the present invention.

19 Claims, No Drawings

(56) References Cited

U.S. PATENT DOCUMENTS

| | | |
|---|---|---|
| 2011/0009622 A1 | 1/2011 | Jitsuoka et al. |
| 2011/0165118 A1 | 7/2011 | Chan et al. |
| 2011/0281950 A1 | 11/2011 | Baiocchi et al. |
| 2012/0009142 A1 | 1/2012 | Karp et al. |
| 2013/0251673 A1 | 9/2013 | Hartman et al. |
| 2013/0267517 A1 | 10/2013 | Guo et al. |
| 2014/0343032 A1 | 11/2014 | Guo et al. |
| 2015/0005295 A1 | 1/2015 | Haché et al. |
| 2015/0119362 A1 | 4/2015 | Gurney et al. |
| 2015/0133428 A1* | 5/2015 | Velaparthi ............ C07D 487/10 514/210.18 |
| 2015/0152073 A1 | 6/2015 | Hartman et al. |
| 2015/0152096 A1 | 6/2015 | Zhang et al. |
| 2015/0197493 A1 | 7/2015 | Hartman et al. |
| 2015/0252057 A1 | 9/2015 | Zhu et al. |
| 2015/0274653 A1 | 10/2015 | Verschueren et al. |
| 2016/0185777 A1 | 6/2016 | Hartman et al. |
| 2016/0206616 A1 | 7/2016 | Zhang et al. |
| 2016/0237078 A9 | 8/2016 | Guo et al. |
| 2016/0264562 A1 | 9/2016 | Liu et al. |
| 2016/0264563 A1 | 9/2016 | Ren et al. |
| 2016/0289212 A1 | 10/2016 | Gao et al. |
| 2016/0296515 A1 | 10/2016 | Han et al. |
| 2016/0332996 A1 | 11/2016 | Gao et al. |
| 2016/0347746 A1 | 12/2016 | Zhang |
| 2017/0014408 A1 | 1/2017 | Gao et al. |
| 2017/0022150 A1 | 1/2017 | Gao et al. |
| 2017/0197986 A1 | 7/2017 | He et al. |
| 2017/0217974 A1 | 8/2017 | Gao et al. |
| 2017/0253609 A1 | 9/2017 | Gao et al. |
| 2017/0355701 A1 | 12/2017 | Qiu et al. |
| 2018/0312512 A1 | 11/2018 | He et al. |
| 2019/0119288 A1 | 4/2019 | Qiu et al. |
| 2019/0177316 A1 | 6/2019 | Qiu et al. |
| 2019/0177320 A1 | 6/2019 | Qiu et al. |

FOREIGN PATENT DOCUMENTS

| | | |
|---|---|---|
| CN | 106928245 A | 7/2017 |
| EP | 2280001 A1 | 2/2011 |
| WO | 8702367 A2 | 4/1987 |
| WO | 9504046 A1 | 2/1995 |
| WO | 0168641 A1 | 9/2001 |
| WO | 0168647 A1 | 9/2001 |
| WO | 2004052852 A1 | 6/2004 |
| WO | 2006033995 A2 | 3/2006 |
| WO | 2008120759 A1 | 10/2008 |
| WO | 2009158473 A1 | 12/2009 |
| WO | 2013006394 A1 | 1/2013 |
| WO | 2013096744 A1 | 6/2013 |
| WO | 2013130703 A2 | 9/2013 |
| WO | 2013144129 A1 | 10/2013 |
| WO | 2013181584 A2 | 12/2013 |
| WO | 2014106019 A2 | 7/2014 |
| WO | 2014184350 A1 | 11/2014 |
| WO | 2014184365 A1 | 11/2014 |
| WO | 2015074546 A1 | 5/2015 |
| WO | 2015113990 A1 | 8/2015 |
| WO | 2015173164 A1 | 11/2015 |
| WO | 2015180631 A1 | 12/2015 |
| WO | 2016016370 A1 | 2/2016 |
| WO | 2016023877 A1 | 2/2016 |
| WO | 2016071215 A1 | 5/2016 |
| WO | 2016107832 A1 | 7/2016 |
| WO | 2016128335 A1 | 8/2016 |
| WO | 2016177655 A1 | 11/2016 |
| WO | 2017013046 A1 | 1/2017 |
| WO | 2017017042 A1 | 2/2017 |
| WO | 2017017043 A1 | 2/2017 |
| WO | 2017061466 A1 | 4/2017 |
| WO | 2017140821 A1 | 8/2017 |
| WO | 2017205115 A1 | 11/2017 |
| WO | 2017216391 A1 | 12/2017 |
| WO | 2017216685 A1 | 12/2017 |
| WO | 2017216686 A1 | 12/2017 |
| WO | 2018001944 A1 | 1/2018 |
| WO | 2018001952 A1 | 1/2018 |
| WO | 2018019297 A1 | 2/2018 |
| WO | 2018022282 A1 | 2/2018 |
| WO | 2018047109 A1 | 3/2018 |
| WO | 2018073753 A1 | 4/2018 |
| WO | 2018083081 A1 | 5/2018 |
| WO | 2018083106 A1 | 5/2018 |
| WO | 2018083136 A1 | 5/2018 |
| WO | 2018085619 A1 | 5/2018 |
| WO | 2018087345 A1 | 5/2018 |
| WO | 2018130152 A1 | 7/2018 |
| WO | 2018144605 A1 | 8/2018 |
| WO | 2018154466 A1 | 8/2018 |
| WO | 2018161960 A1 | 9/2018 |
| WO | 2018181883 A1 | 10/2018 |
| WO | 2018196805 A1 | 11/2018 |
| WO | 2018198079 A1 | 11/2018 |
| WO | 2018219356 A1 | 12/2018 |
| WO | 2019069293 A1 | 4/2019 |
| WO | 2019097479 A1 | 5/2019 |
| WO | 2019110352 A1 | 6/2019 |
| WO | 2019123285 A1 | 6/2019 |
| WO | 2019129681 A1 | 7/2019 |
| WO | 2019166951 A1 | 9/2019 |

OTHER PUBLICATIONS

Chemical Abstract Service STN CAplus [online database], Accession No. 2003:1014580. (Year: 2003).

Chemical Abstract Service STN Database Registry No. 1578268-77-5 [online][Entered STN: Apr. 1, 2014].

Chemical Abstracts Registry No. 1026741-09-2, indexed in the Registry file on Jun. 9, 2008.

Chemical Abstracts Registry No. 115280-56-3, indexed in the Registry file on STN CAS Online Jul. 16, 1988.

Chemical Abstracts Registry No. 1269203-67-9, indexed in the Registry file on STN CAS Online Mar. 21, 2011.

Chemical Abstracts Registry No. 1350251-34-1, indexed in the Registry file on STN CAS Online Dec. 7, 2011.

Chemical Abstracts Registry No. 397288-41-1, indexed in the Registry file on Mar. 1 (Year: 2002).

Chemical Abstracts Registry No. 792901-47-4, indexed in the Registry file on STN CAS Online Dec. 6, 2004.

Chemical Abstracts Registry No. 92555-24-3, indexed in the Registry file on Dec. 17, 1984.

Chemical Abstracts Registry No. 950067-32-0, indexed in the Registry file on Oct. 10, 2007.

PubChem CID 57036978, National Center for Biotechnology Information. PubChem Compound Database; CID=57036978, https://pubchem.ncbi.nlm.nih.gov/compound/57036978 (accessed May 19, 2017), create date Jun. 13, 2012.

PubChem CID 69095846 {National Center for Biotechnology Information. PubChem Compound Database; CID=69095846, https://pubchem.ncbi.nlm.nih.gov/compound/69095846 (accessed May 23, 2017), create date Nov. 30, 2012.

PubChem CI D 10194182, National Center for Biotechnology Information. PubChem Compound Database; CI 0=10194182, https://pubchem.ncbi.nlm.nih.gov/compound/10194182 (accessed May 19, 2017), create date Oct. 25, 2006.

Pubchem-'428' Create Date: Sep. 11, 2005 (Sep. 11, 2005) Date Accessed: Jun. 17, 2016.

Pubchem-CID 23201920, Create Date: Dec. 5, 2007, p. 3.

Pubchem-CID 63186259, Create Date: Oct. 22, 2012 (Oct. 22, 2012) p. 3.

Pubchem-SID 15224030 Deposit Date: Oct. 25, 2006.

Pubchern-57224610 ('610') Create Date: Jun. 14, 2012 (Jun. 14, 2012) Date Accessed: Jun. 17, 2016.

Ballatore, C. et al., "Carboxylic Acid (Bio)Isosteres in Drug Design", ChemMedChem., vol. 8, No. 3, 2013, 385-395.

Clark, M. T. et al., "5-(aLKYLSULFONYL)Salicylanilides as Potential Dental Antiplaque Agents", Journal of Medicinal Chemistry, 29(1), 1986, 25-29.

(56) References Cited

OTHER PUBLICATIONS

Janetka, J. W. et al., "Discovery of a novel class of 2-ureido thiophene carboxamide checkpoint kinase inhibitors", Bioorganic & Medicinal Chemistry Letters, 18, 2008, 4242-4248.
Li et al., 8 ACS Medicinal Chemistry Letters, 8, 2017, 969-974.
Noguchi, Chiemi et al., "G to a Hypermutation of Hepatitis B Virus", Hepatology, vol. 41, No. 3, 2005, 2005, 626-633.
Yang, et al., "Enzyme-mediated hydrolytic activation of prodrugs", Acta Pharmaceutica Sinica B., vol. 1(3), Sep. 9, 2011, 143-159.
CAS Abstract and Indexed Compounds WO 01/68647 (2001), 2001.
, "N-[4-(cyanomethyl)phenyl]-5-(hexyhydro-1-H-azepine-1-yl)sulfonyl]-2-methoxy-benzamid e", Database Registry [Online] Chemical Abstracts Service, Columbus, Ohio, US; May 6, 2011 (May 6, 2011), XP55358935,accession No. RN:1291044-81-9.
Das, Jagabandhu et al., "Discovery of 2-Amino-heteroaryl-benzothiazole-6-anilides as Potent p56lck Inhibitors", Biorganic & Medicinal Chemistry Letters, 13, 2003, 2587-2590.
El-Hamouly, Wageeh S. et al., "Synthesis and Antimicrobial Activity of New 3, 4-Dihydropyrimidinones", International Journal of Pharmaceutical Sciences and Research, vol. 2, 2011, 1054-1062.
Qiu, Zongxing et al., "Design and Synthesis of Orally Bioavailable 4-Methyl Heteroaryldihydropyrimidine Based Hepatitis B Virus (HBV) Capsid Inhibitors", Journal of Medicinal Chemistry, 2016.

\* cited by examiner

HEPATITIS B ANTIVIRAL AGENTS

RELATED APPLICATIONS

This application claims the benefit of U.S. Provisional Application No. 62/649,993, filed on Mar. 29, 2018. The entire teachings of the above application are incorporated herein by reference.

TECHNICAL FIELD

The present invention relates generally to novel antiviral agents. Specifically, the present invention relates to compounds which can inhibit the protein(s) encoded by hepatitis B virus (HBV) or interfere with the function of the HBV life cycle, compositions comprising such compounds, methods for inhibiting HBV viral replication, methods for treating or preventing HBV infection, and processes for making the compounds.

BACKGROUND OF THE INVENTION

HBV infection remains a major public health problem, affecting approximately 2 billion people worldwide. Among them, 350 million people worldwide and 1.4 million in the US develop a chronic infection, which can lead to chronic persistent hepatitis, liver cirrhosis, and hepatocellular carcinoma (HCC). Every year 500,000 to 1 million people die from the end stage of liver diseases caused by HBV infection.

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent HCC. Current therapy goals for HBV-infected patients are directed to reducing serum HBV DNA to low or undetectable levels, and to ultimately reducing or preventing the development of cirrhosis and HCC.

The HBV is an enveloped, partially double-stranded DNA (dsDNA) virus of the hepadnavirus family (Hepadnaviridae). HBV capsid or core protein (CP) plays essential roles in HBV replication. The predominant biological function of capsid protein is to act as a structural protein to encapsidate pre-genomic RNA and form immature capsid particles, which spontaneously self-assemble from many copies of core dimers in the cytoplasm. Capsid protein also regulates viral DNA synthesis through different phosphorylation status of its C-terminal phosphorylation sites. Also, capsid protein might facilitate the nuclear translocation of viral relaxed circular genome by means of the nuclear localization signals located in the Arginine-rich domain of the C-terminal region of capsid protein. In the nucleus, as a component of viral cccDNA minichromosome, capsid protein could play a structural and regulatory role in the functionality of cccDNA minichromosomes. Capsid protein also interacts with viral large envelope protein in endoplasmic reticulum (ER) and triggers the release of intact viral particles from hepatocytes.

Capsid related anti-HBV inhibitors have been reported. For example, phenylpropen-amide derivatives, including compounds named AT-61 and AT-130 (Feld J. et al. Antiviral Res. 2007, 76, 168), and a class of thiazolidin-4-ones from Valeant (WO 2006/033995), have been shown to inhibit pregenomic RNA (pgRNA) packaging. Heteroaryldihydropyrimidines or HAPs were discovered in a tissue culture-based screening (Weber et al., Antiviral Res. 2002, 54, 69). These HAP analogs act as synthetic allosteric activators and are able to induce aberrant capsid formation that leads to degradation of the core protein. A subclass of sulphamoylarylamides shows activity against HBV (WO2013/006394, WO2013/096744, WO2014/184365, and WO 2017/136403). It was also shown that the small molecule bis-ANS acts as a molecular 'wedge' and interferes with normal capsid-protein geometry and capsid formation (Zlotnick A. et al. J. Virol. 2002, 4848).

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

The present invention relates to novel antiviral compounds, pharmaceutical compositions comprising such compounds, as well as methods to treat or prevent viral (particularly HBV) infection in a subject in need of such therapy with said compounds. Compounds of the present invention inhibit the protein(s) encoded by hepatitis B virus (HBV) or interfere with the life cycle of HBV and are useful as antiviral agents. In addition, the present invention includes methods for preparing the compounds of the invention.

In its principal aspect, the present invention provides a compound of Formula (I):

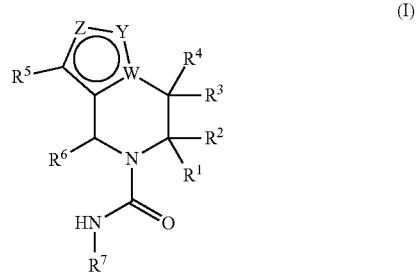

(I)

or a pharmaceutically acceptable salt thereof, wherein:

W and Y are each N and Z is $CR^{10}$; or W is C, one of Y and Z is N and the other is $NR^{11}$; $R^{10}$ is hydrogen, halo, or optionally substituted $C_1$-$C_6$ alkyl; $R^{11}$ is hydrogen, optionally substituted $C_1$-$C_6$ alkyl, or optionally substituted $C_3$-$C_8$ cycloalkyl; or W, Y and Z are each N; preferably W and Y are N, and Z is CH; or W is C, one of Y and Z is N, and the other is NH or optionally substituted NMe; or W, Y and Z are each N.

$R^1$ and $R^3$ are independently hydrogen or optionally substituted $C_1$-$C_6$ alkyl; preferably $R^1$ and $R^3$ are hydrogen or optionally substituted methyl;

$R^2$ is selected from a group consisting of optionally substituted $C_3$-$C_6$ cycloalkyl, optionally substituted $C_3$-$C_8$ cycloalkenyl, optionally substituted 3- to 8-membered heterocyclic, optionally substituted aryl, and optionally substituted heteroaryl;

$R^4$ is selected from the group consisting of hydrogen, halo, hydroxy, protected hydroxy, amino, optionally substituted amino, optionally substituted $C_1$-$C_6$ alkyl, and optionally substituted $C_1$-$C_6$ alkoxy;

Alternatively, $R^1$ and $R^3$ are taken together with the carbon atoms to which they are attached to form an olefinic double bond;

Alternatively, $R^1$ and $R^2$ are taken together with the carbon atom to which they are attached to form a group consisting of optionally substituted $C_3$-$C_8$ cycloalkyl, optionally substituted $C_3$-$C_8$ cycloalkenyl, or optionally substituted 3- to 8-membered heterocyclic;

Alternatively, $R^2$ and $R^4$ are taken together with the carbon atoms to which they are attached to form optionally substituted $C_3$-$C_8$ cycloalkyl, optionally substituted $C_3$-$C_8$ cycloalkenyl, or optionally substituted 3- to 8-membered heterocyclic;

Alternatively, $R^1$, $R^2$, $R^3$ and $R^4$ are taken together with the carbon atoms to which they are attached to form optionally substituted aryl or optionally substituted heteroaryl;

Alternatively, $R^3$ and $R^4$ are taken together with the carbon atom to which they are attached to form optionally substituted $C_3$-$C_8$ cycloalkyl, optionally substituted $C_3$-$C_8$ cycloalkenyl, or optionally substituted 3- to 8-membered heterocyclic;

$R^5$ is selected from the group consisting of optionally substituted $C_1$-$C_6$ alkyl, optionally substituted $C_2$-$C_8$ alkenyl, optionally substituted $C_2$-$C_8$ alkynyl, optionally substituted $C_3$-$C_8$ cycloalkyl, optionally substituted 3- to 8-membered heterocyclic, optionally substituted aryl, optionally substituted heteroaryl, and -L-$R^{12}$; wherein L is selected from the group consisting of —O—, —S—, —$NR^{11}$—, —C(O)—, —C(O)O—, —OC(O)—, —C(O)N($R^{11}$)—, —N($R^{11}$)C(O)—, —OC(O)N($R^{11}$)—, —N($R^{11}$)C(O)O—, —N($R^{11}$)C(O)N($R^{11}$)—, —S(O)—, —S(O)$_2$—, —S(O)$_2$N($R^{11}$)—, —N($R^{11}$)S(O)$_2$—, optionally substituted $C_1$-$C_6$ alkyl, optionally substituted $C_2$-$C_8$ alkenyl, optionally substituted $C_2$-$C_8$ alkynyl, optionally substituted $C_3$-$C_8$ cycloalkyl, optionally substituted 3- to 8-membered heterocyclic, optionally substituted aryl, and optionally substituted heteroaryl; and $R^{12}$ is selected from the group consisting of hydrogen, optionally substituted $C_1$-$C_6$ alkyl, optionally substituted $C_3$-$C_8$ cycloalkyl, optionally substituted 3- to 8-membered heterocyclic, optionally substituted aryl, and optionally substituted heteroaryl;

$R^6$ is hydrogen or optionally substituted $C_1$-$C_6$ alkyl; and $R^7$ is optionally substituted aryl, optionally substituted heteroaryl, optionally substituted $C_1$-$C_6$ alkyl, or optionally substituted $C_3$-$C_8$ cycloalkyl.

Each preferred group stated above can be taken in combination with one, any or all other preferred groups.

DETAILED DESCRIPTION OF THE INVENTION

In one embodiment of the present invention is a compound of Formula (I) described above, or a pharmaceutically acceptable salt thereof.

In one embodiment, W and Y are each N and Z is $CR^{10}$. In certain embodiments, W and Y are each N and Z is CH.

In certain embodiments, W is C, one of Y and Z is N and the other is $NR^{11}$. In certain embodiments, W is C, one of Y and Z is N and the other is $NR^{11}$, where $R_{11}$ is hydrogen or optionally substituted methyl.

In certain embodiments, W, Y and Z are each N.

In certain embodiments, the present invention relates to compounds of Formula (I) and pharmaceutically acceptable slats thereof, wherein $R^1$, $R^3$ and $R^6$ are independently hydrogen or optionally substituted $C_1$-$C_6$ alkyl. In certain embodiments, $R^1$, $R^3$ and $R^6$ are independently hydrogen or optionally substituted methyl.

In certain embodiments the present invention relates to compounds of Formula (I), and pharmaceutically acceptable salts thereof, wherein $R^5$ is -L-$R^{12}$; wherein L is selected from the group consisting of —O—, —S—, —$NR^{11}$—, —C(O)—, —C(O)O—, —OC(O)—, —C(O)N($R^{11}$)—, —N($R^{11}$)C(O)—, —OC(O)N($R^{11}$)—, —N($R^{11}$)C(O)O—, —N($R^{11}$)C(O)N($R^{11}$)—, —S(O)—, —S(O)$_2$—, —S(O)$_2$N($R^{11}$)—, and —N($R^{11}$)S(O)$_2$—; $R^{11}$ and $R^{12}$ are previously defined.

In certain embodiments the present invention relates to compounds of Formula (I), and pharmaceutically acceptable salts thereof, wherein $R^5$ is optionally substituted phenyl or optionally substituted heteroaryl. In certain embodiments, $R^5$ is phenyl or heteroaryl substituted with one or more substituents, such as 1, 2, 3, 4 or 5 substituents. Preferably the substituents are independently selected from halogen, CN, optionally substituted —$C_1$-$C_3$ alkoxy, optionally substituted —$C_1$-$C_3$ alkyl, and optionally substituted —$C_3$-$C_6$ cycloalkyl. In certain embodiments, $R^5$ is phenyl or heteroaryl substituted with one or more substituents independently selected from fluoro, chloro, bromo, methyl, difluoromethyl, trifluoromethyl, CN and cyclopropyl.

In certain embodiments the present invention relates to compounds of Formula (I), and pharmaceutically acceptable salts thereof, wherein $R^5$ is an aryl or heteroaryl group derived from one of the following by removal of one hydrogen atom:

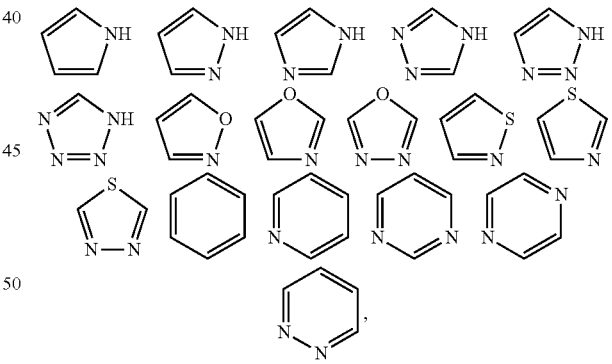

wherein each of the above shown groups is optionally substituted, and is connected to the pyrazole or triazole ring through a carbon atom or, where possible, a nitrogen atom. In certain embodiments, each of these groups independently selected from halogen and $C_1$-$C_4$-alkyl.

In certain embodiments, the present invention relates to compounds of Formula (I), and pharmaceutically acceptable salts thereof, wherein $R^5$ is optionally substituted 3- to 8-membered heterocyclic.

In certain embodiments the present invention relates to compounds of Formula (I), and pharmaceutically acceptable salts thereof, wherein $R^5$ is a heterocyclic group derived from one of the following by removal of one hydrogen atom:

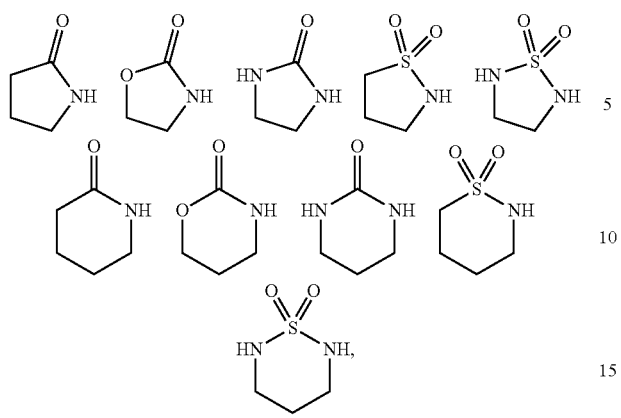

wherein each of the above shown groups is optionally substituted, and is connected to the pyrazole or triazole ring through a carbon or nitrogen atom. In certain embodiments, each of these groups is connected to the pyrazole or triazole ring through a nitrogen atom. In certain embodiments, each of these groups is substituted with one or more substituents independently selected from $C_1$-$C_6$-alkyl, aryl, heteroaryl, $C_3$-$C_6$-cycloalkyl, spiro-$C_3$-$C_6$-cycloalkyl and fused $C_3$-$C_6$-cycloalkyl.

In certain embodiments, the present invention relates to compounds of Formula (I), and their pharmaceutically acceptable salts thereof, wherein $R^7$ is optionally substituted phenyl. In certain embodiments, $R^7$ is phenyl substituted with one or more substituents, such as 1, 2, 3, 4 or 5 substituents. Preferably the substituents are independently selected from halogen, CN, optionally substituted —$C_1$-$C_3$ alkoxy, optionally substituted —$C_1$-$C_3$ alkyl, and optionally substituted —$C_3$-$C_6$ cycloalkyl. In certain embodiments, $R^7$ is phenyl substituted with one or more substituents independently selected from fluoro, chloro, bromo, methyl, difluoromethyl, trifluoromethyl, CN, methoxy, hydroxyl, isopropyl and cyclopropyl. In certain embodiments, $R^7$ is selected from the groups below:

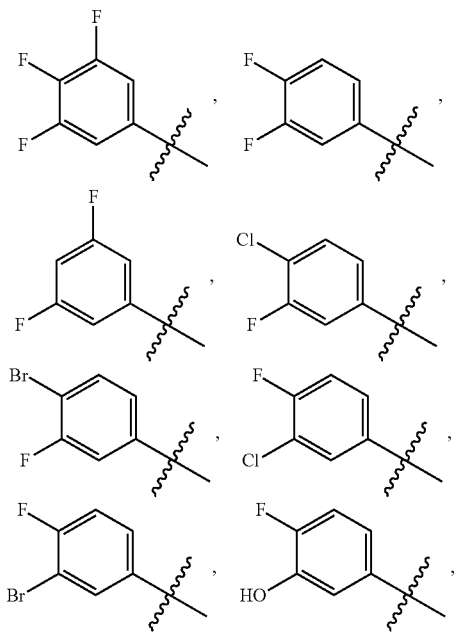

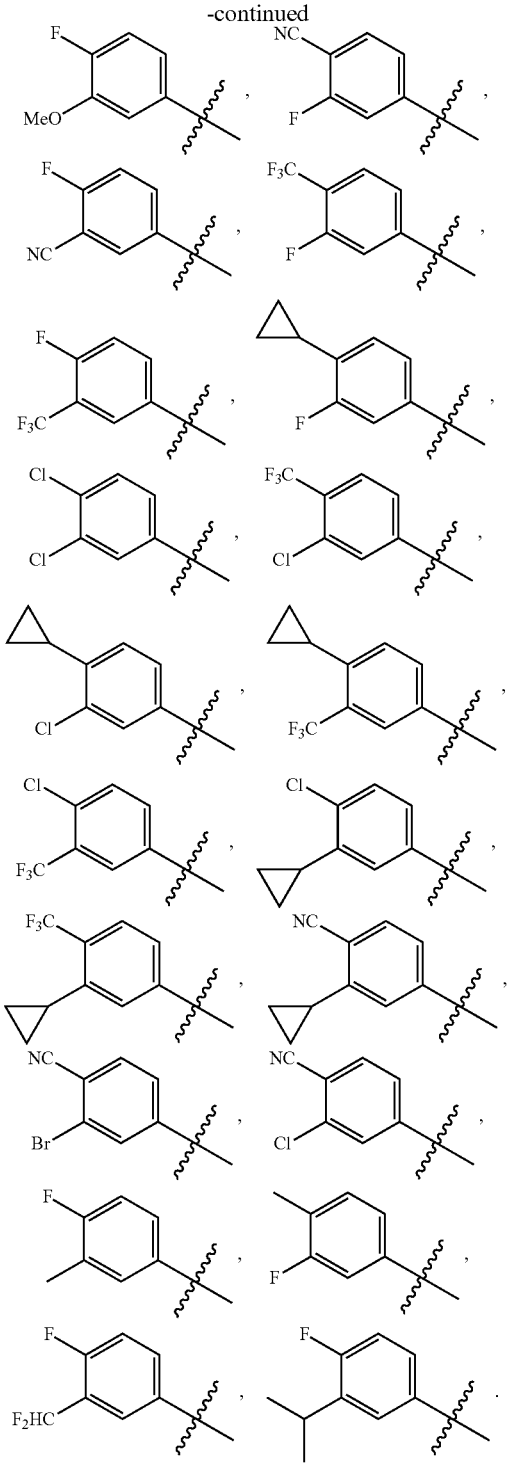

In certain embodiments, the present invention relates to compounds of Formula (I), and pharmaceutically acceptable salts thereof, wherein $R^7$ is optionally substituted monocyclic heteroaryl. In certain embodiments, the present invention relates to compounds of Formula (I) or, and pharmaceutically acceptable salts thereof, wherein $R^7$ is optionally substituted thiophenyl, optionally substituted thiazolyl, optionally substituted pyridyl, or optionally substituted pyrimidinyl. In certain embodiments, the present invention relates to compounds of Formula (I) and pharmaceutically acceptable salts thereof, wherein $R^7$ is optionally substituted pyrimidinyl, optionally substituted pyridazyl, or optionally substituted pyrazyl as shown below:

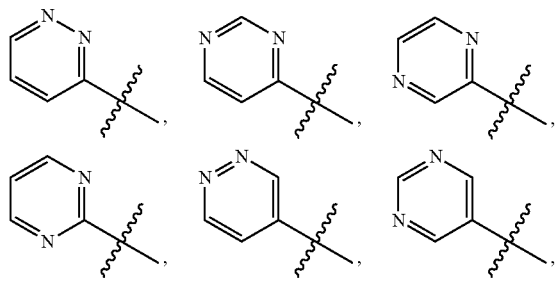

In certain embodiments, the present invention relates to compounds of Formula (I), and pharmaceutically acceptable salts thereof, wherein $R^7$ is optionally substituted bicyclic heteroaryl. In certain embodiments, the present invention relates to compounds of Formula (I), and pharmaceutically acceptable salts thereof, wherein $R^7$ is optionally substituted 5/6 or 6/6 bicyclic heteroaryl. In certain embodiments, $R^7$ is optionally substituted 5/6 bicyclic heteroaryl and is connected to the nitrogen atom of —NH(CO)— through a carbon atom of the 6-membered ring of said 5/6 bicyclic heteroaryl. In certain embodiments, the present invention relates to compounds of Formula (I), and pharmaceutically acceptable salts thereof, wherein $R^7$ is optionally substituted benzimidazolyl, benzothiazolyl, benzoxazolyl, indazolyl, quinolyl, isoquinolyl or quinazolyl.

In certain embodiments, the present invention relates to compounds of Formula (I), and pharmaceutically acceptable salts thereof, wherein $R^7$ is optionally substituted $C_1$-$C_6$ alkyl or optionally substituted $C_3$-$C_8$ cycloalkyl.

In certain embodiments, the present invention relates to compounds of Formula (I) and pharmaceutically acceptable salts thereof, wherein $R^1$ and $R^2$ are taken together with the carbon atom to which they are attached to form an optionally substituted $C_3$-$C_8$ cycloalkyl, optionally substituted $C_3$-$C_8$ cycloalkenyl, or optionally substituted 3- to 8-membered heterocyclic. In certain embodiments, $R^1$, $R^2$ and the carbon atom to which they are attached form a $C_3$-$C_5$ cycloalkyl.

In certain embodiments, the present invention relates to compounds of Formula (Ia), and pharmaceutically acceptable salts thereof,

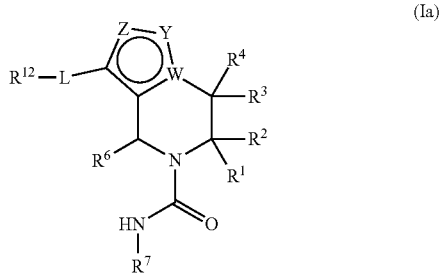

wherein L, W, Y, Z, $R^1$, $R^2$, $R^3$, $R^4$, $R^6$, $R^7$, and $R^{12}$ are as previously defined.

In certain embodiments the present invention relates to compounds of Formula (Ia), and pharmaceutically acceptable salts thereof, wherein L is —O—, —N($R^{11}$)C(O)—, —OC(O)N($R^{11}$)—, —N($R^{11}$)C(O)O—, —N($R^{11}$)C(O)N($R^{11}$)—, or —N($R^{11}$)S(O)$_2$—.

In certain embodiments the present invention relates to compounds of Formula (Ia), and pharmaceutically acceptable salts thereof, wherein L is optionally substituted phenyl or optionally substituted heteroaryl. In certain embodiments the present invention relates to compounds of Formula (Ia), and pharmaceutically acceptable salts thereof, wherein L is optionally substituted $C_3$-$C_8$ cycloalkyl or optionally substituted 3- to 8-membered heterocyclic.

In certain embodiments the present invention relates to compounds of Formula (Ia), and pharmaceutically acceptable salts thereof, wherein L is an aryl or heteroaryl group derived from one of the following by removal of two hydrogen atoms:

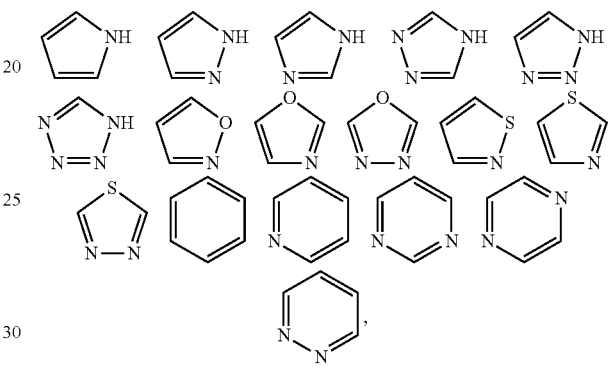

wherein each of the above shown groups is optionally substituted and is connected to the remainder of the molecule through carbon or, where possible, nitrogen atoms.

In certain embodiments the present invention relates to compounds of Formula (Ia), and pharmaceutically acceptable salts thereof, wherein L is a heterocyclic group derived from one of the following by removal of two hydrogen atoms:

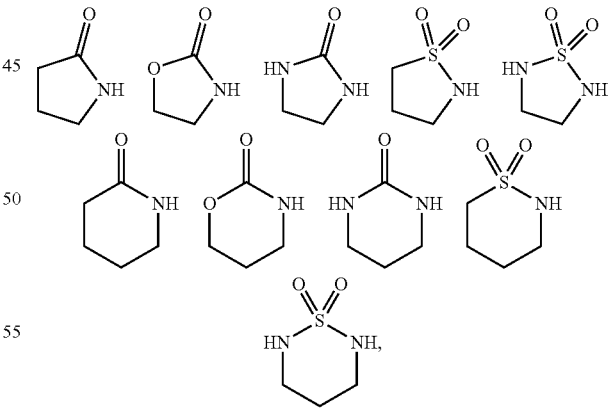

wherein each of the above shown groups is optionally substituted and is connected to the remainder of the molecule through carbon or nitrogen atoms.

In certain embodiments the present invention relates to compounds of Formula (Ia), and pharmaceutically acceptable salts thereof, wherein $R^{12}$ is an aryl or heteroaryl group derived from one of the following by removal of one hydrogen atom:

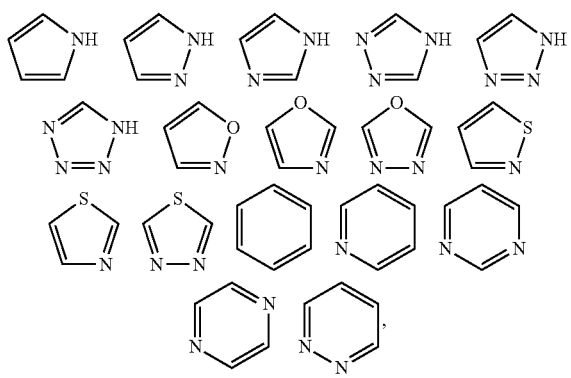

wherein each of the above shown groups is optionally substituted and is connected to L through a carbon atom or, where possible, a nitrogen atom.

In certain embodiments the present invention relates to compounds of Formula (Ia), and pharmaceutically acceptable salts thereof, wherein $R^{12}$ is a heterocyclic group derived from one of the following by removal of one hydrogen atom:

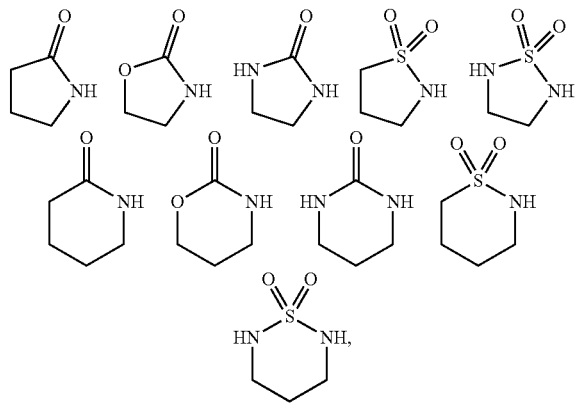

wherein each of the above shown groups is optionally substituted and is connected to L through a carbon atom or a nitrogen atom.

In certain embodiments, the present invention relates to compounds of Formula (II), and pharmaceutically acceptable salts thereof,

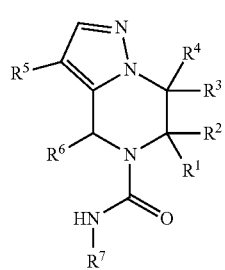

(II)

wherein $R^1$, $R^2$, $R^3$, $R^4$, $R^5$, $R^6$, and $R^7$ are as previously defined.

In certain embodiments, the present invention relates to compounds of Formula (II), and pharmaceutically acceptable salts thereof, wherein $R^2$ is selected from a group consisting of optionally substituted $C_3$-$C_8$ cycloalkyl, optionally substituted $C_3$-$C_8$ cycloalkenyl, optionally substituted 3- to 8-membered heterocyclic, optionally substituted aryl, and optionally substituted heteroaryl.

In certain embodiments, the present invention relates to compounds of Formula (II), and pharmaceutically acceptable salts thereof, wherein $R^2$ and $R^4$ are taken together with the carbon atoms to which they are attached to form optionally substituted $C_3$-$C_8$ cycloalkyl, optionally substituted $C_3$-$C_8$ cycloalkenyl, or optionally substituted 3- to 8-membered heterocyclic. In certain embodiments, the present invention relates to compounds of Formula (II), and pharmaceutically acceptable salts thereof, wherein $R^1$, $R^2$, $R^3$ and $R^4$ are taken together with the carbon atoms to which they are attached to form optionally substituted aryl or optionally substituted heteroaryl.

In certain embodiments, the present invention relates to compounds of Formula (IIa), and pharmaceutically acceptable salts thereof,

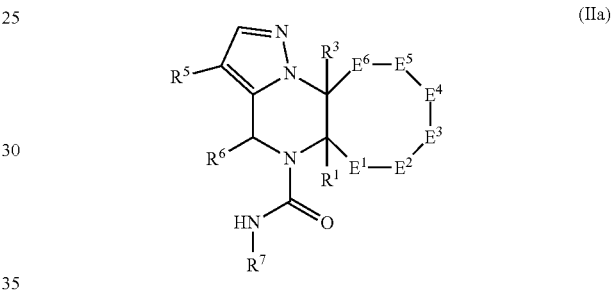

(IIa)

wherein at least one of $E^1$, $E^2$, $E^3$, $E^4$, $E^5$, and $E^6$ is present, and $E^1$, $E^2$, $E^3$, $E^4$, $E^5$, and $E^6$ are each independently selected from the group consisting of absent, —$CR^{13}R^{14}$—, —$NR^{11}$—, —O—, —C(O)—, —S(O)—, —S(O)$_2$—, and —S—; $R^{13}$ and $R^{14}$ at each occurrence are independently selected from the group consisting of hydrogen, halo, and optionally substituted $C_1$-$C_6$ alkyl; $R^1$, $R^3$, $R^5$, $R^6$, $R^7$, and $R^{11}$ are as previously defined.

In certain embodiments, $E^1$-$E^6$ together form —(CH$_2$)$_n$—, where n is 1 to 6. Preferably n is 1 to 4, and more preferably n is 3. In certain embodiments, $E^1$-$E^6$ together form —(CH$_2$)$_o$—U—(CH$_2$)$_p$—, where o and p are each independently 0 to 3, provided that the sum of o and p is 2 to 5, and U is —$NR^{11}$—, —O—, —C(O)—, —S(O)—, —S(O)$_2$—, or —S—.

In certain embodiments, compounds of Formula (IIa) have the stereochemistry shown in Formula (IIa-1) or Formula (IIa-2):

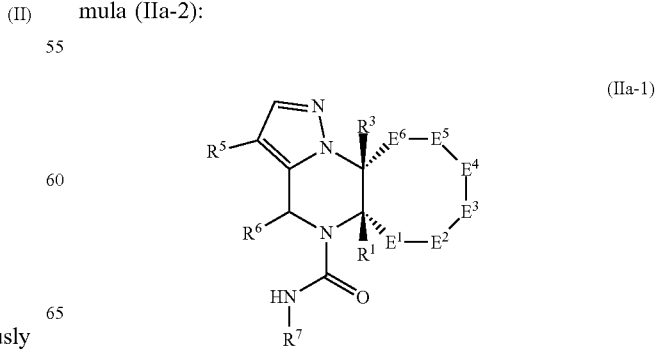

(IIa-1)

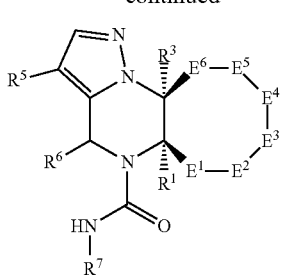
(IIa-2)

In preferred embodiments, compounds of Formula (IIa) have the stereochemistry shown in Formula (IIa-1).

In certain embodiments, compounds of Formula (IIa) can have the stereochemistry shown in Formula (IIa-3) or Formula (IIa-4),

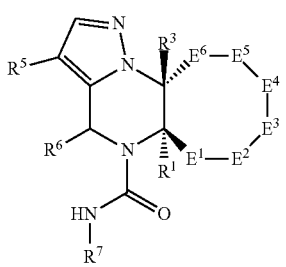
(IIa-3)

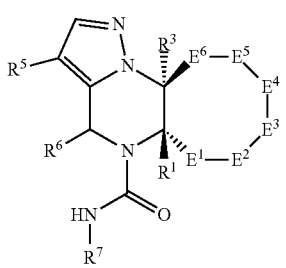
(IIa-4)

In certain embodiments, the present invention relates to compounds of Formula (III) or Formula (IV), and pharmaceutically acceptable salts thereof,

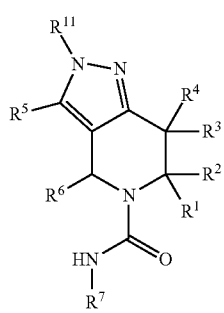
(III)

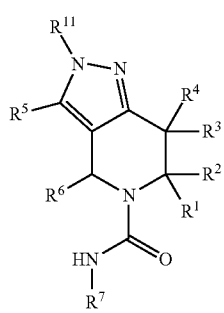
(IV)

wherein $R^1$, $R^2$, $R^3$, $R^4$, $R^5$, $R^6$, $R^7$, and $R^{11}$ are as previously defined.

In certain embodiments, the present invention relates to compounds of Formula (III), or Formula (IV), and pharmaceutically acceptable salts thereof, wherein $R^2$ is selected from a group consisting of optionally substituted $C_3$-$C_8$ cycloalkyl, optionally substituted $C_3$-$C_8$ cycloalkenyl, optionally substituted 3- to 8-membered heterocyclic, optionally substituted aryl, and optionally substituted heteroaryl.

In certain embodiments, the present invention relates to compounds of Formula (III), or Formula (IV), and pharmaceutically acceptable salts thereof, wherein $R^2$ and $R^4$ are taken together with the carbon atoms to which they are attached to form optionally substituted $C_3$-$C_8$ cycloalkyl, optionally substituted $C_3$-$C_8$ cycloalkenyl, or optionally substituted 3- to 8-membered heterocyclic. In certain embodiments, the present invention relates to compounds of Formula (III) or Formula (IV), and pharmaceutically acceptable salts thereof, wherein $R^1$, $R^2$, $R^3$ and $R^4$ are taken together with the carbon atoms to which they are attached to form optionally substituted aryl or optionally substituted heteroaryl.

In certain embodiments, the present invention relates to compounds of Formula (IIIa) or Formula (IVa), and pharmaceutically acceptable salts thereof,

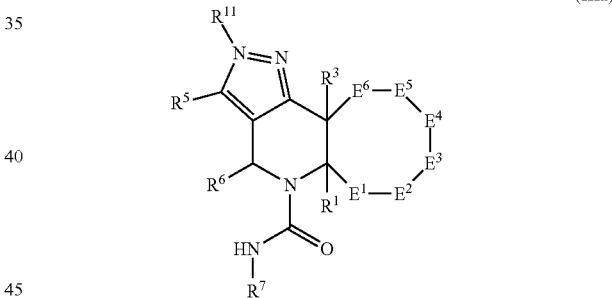

(IIIa)

(IVa)

wherein $E^1$, $E^2$, $E^3$, $E^4$, $E^5$, $E^6$, $R^1$, $R^3$, $R^5$, $R^6$, $R^7$, and $R^{11}$ are as previously defined.

In certain embodiments, compounds of Formula (IIIa) and Formula (IVa) can have the stereochemistry shown in Formula (IIIa-1) or Formula (IIIa-2) and Formula (IVa-1) or Formula (IVa-2) respectively.

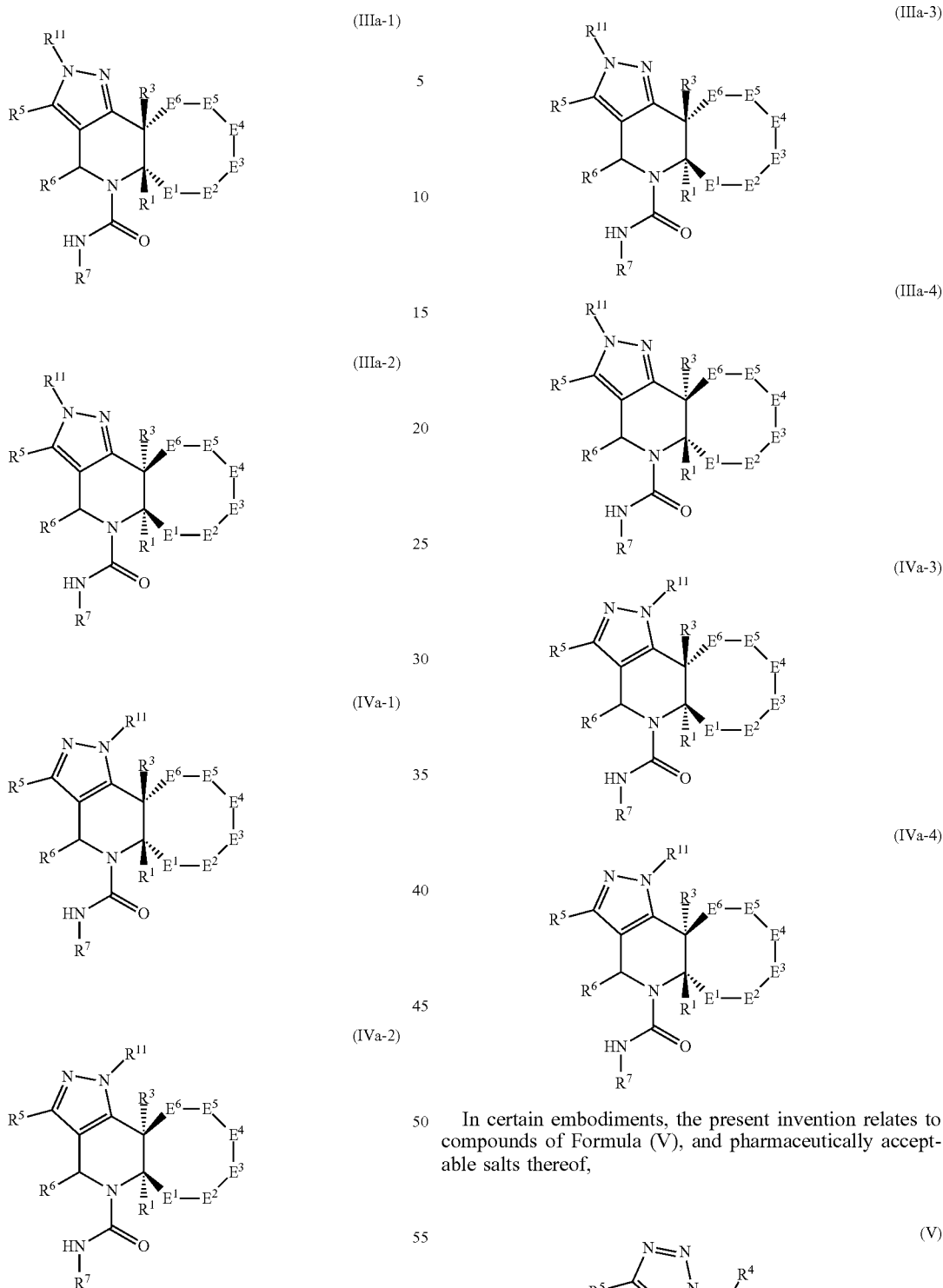

In preferred embodiments, compounds of Formula (IIIa) and Formula (IVa) have the stereochemistry shown in Formula (IIIa-1) and Formula (IVa-1) respectively.

In certain embodiments, compounds of Formula (IIIa) and Formula (IVa) can have the stereochemistry shown in Formula (IIIa-3) or Formula (IIIa-4) and Formula (IVa-3) or Formula (IVa-4).

In certain embodiments, the present invention relates to compounds of Formula (V), and pharmaceutically acceptable salts thereof,

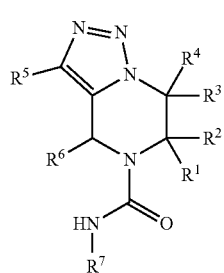

wherein $R^1$, $R^2$, $R^3$, $R^4$, $R^5$, $R^6$, and $R^7$ are as previously defined.

In certain embodiments, the present invention relates to compounds of Formula (V), and pharmaceutically acceptable salts thereof, wherein $R^2$ is selected from a group consisting of optionally substituted $C_3$-$C_8$ cycloalkyl, optionally substituted $C_3$-$C_8$ cycloalkenyl, optionally substituted 3- to 8-membered heterocyclic, optionally substituted aryl, and optionally substituted heteroaryl.

In certain embodiments, the present invention relates to compounds of Formula (V), and pharmaceutically acceptable salts thereof, wherein $R^2$ and $R^4$ are taken together with the carbon atoms to which they are attached to form optionally substituted $C_3$-$C_8$ cycloalkyl, optionally substituted $C_3$-$C_8$ cycloalkenyl, or optionally substituted 3- to 8-membered heterocyclic. In certain embodiments, the present invention relates to compounds of Formula (V), and pharmaceutically acceptable salts thereof, wherein $R^1$, $R^2$, $R^3$ and $R^4$ are taken together with the carbon atoms to which they are attached to form optionally substituted aryl or optionally substituted heteroaryl.

In certain embodiments, the present invention relates to compounds of Formula (Va), and pharmaceutically acceptable salts thereof,

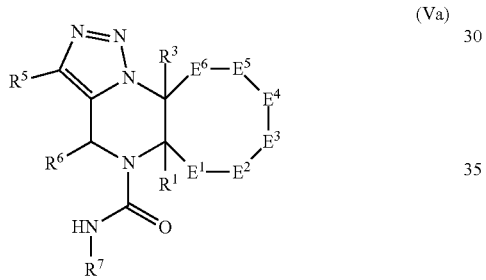

(Va)

wherein at least one of $E^1$, $E^2$, $E^3$, $E^4$, $E^5$, and $E^6$ is present, and $E^1$, $E^2$, $E^3$, $E^4$, $E^5$, and $E^6$ are each independently selected from the group consisting of absent, —$CR^{13}R^{14}$—, —$NR^{11}$—, —O—, —C(O)—, —S(O)—, —S(O)$_2$—, and —S—; $R^{13}$ and $R^{14}$ at each occurrence are independently selected from the group hydrogen, halo, or optionally substituted $C_1$-$C_6$ alkyl; $R^1$, $R^3$, $R^5$, $R^6$, $R^7$, and $R^{11}$ are as previously defined.

In certain embodiments, compounds of Formula (Va) have the stereochemistry shown in Formula (Va-1) or Formula (Va-2):

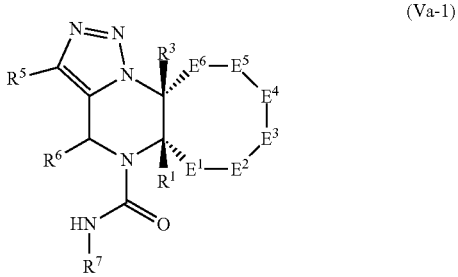

(Va-1)

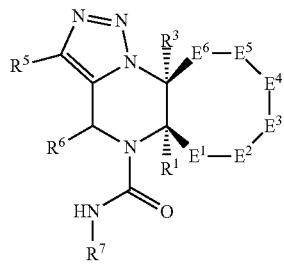

(Va-2)

In preferred embodiments, compounds of Formula (Va) have the stereochemistry shown in Formula (Va-1).

In certain embodiments, compounds of Formula (Va) can have the stereochemistry shown in Formula (Va-3) or Formula (Va-4),

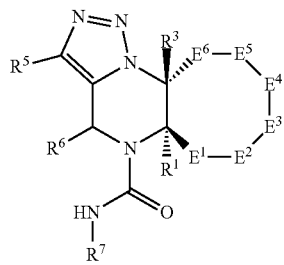

(Va-3)

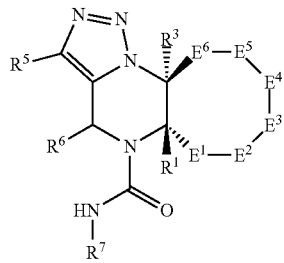

(Va-4)

In certain embodiments, the present invention relates to compounds of Formula (VI), and pharmaceutically acceptable salts thereof,

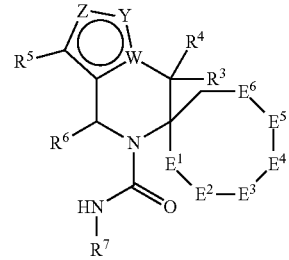

(VI)

wherein W, Y, Z, $E^1$, $E^2$, $E^3$, $E^4$, $E^5$, $E^6$, $R^1$, $R^3$, $R^5$, $R^6$, and $R^7$ are as previously defined.

In certain embodiments, the present invention relates to compounds of Formula (VIIa), Formula (VIIb), Formula (VIIc), or Formula (VIId), and pharmaceutically acceptable salts thereof,

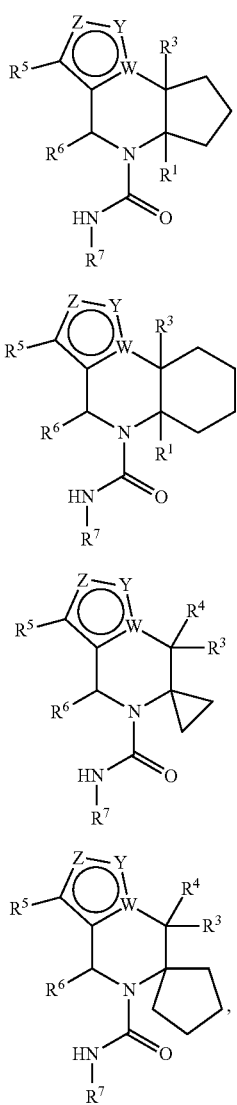
(VIIa)
(VIIb)
(VIIc)
(VIId)
wherein W, Y, Z, $R^1$, $R^3$, $R^4$, $R^5$, and $R^7$ are as previously defined.
In certain embodiments, the present invention relates to compounds of Formula (VIIa), Formula (VIIb), Formula (VIIc), or Formula (VIId), and pharmaceutically acceptable salts thereof, wherein $R^7$ is selected from the groups below:
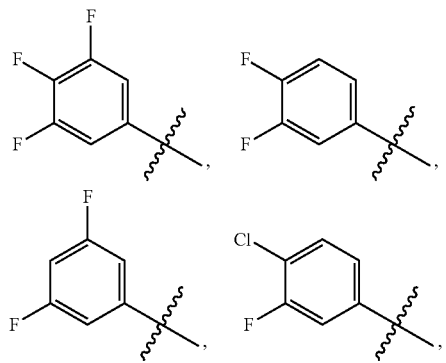
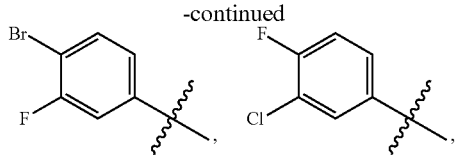
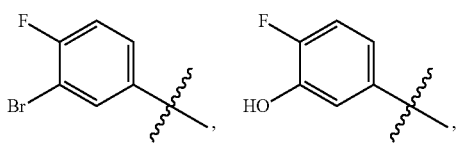
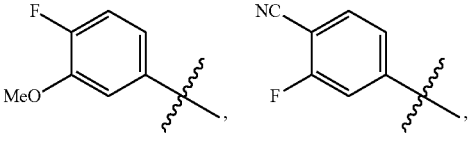
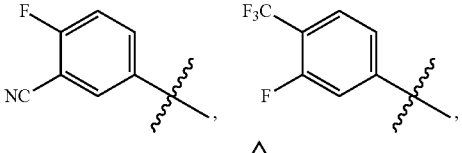
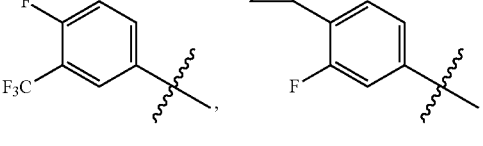
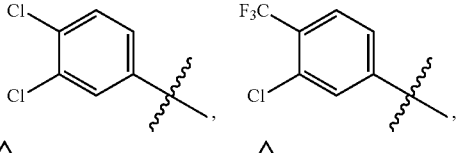
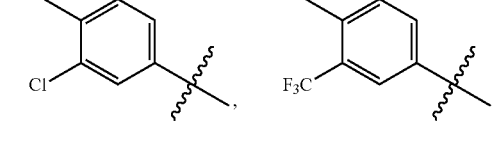
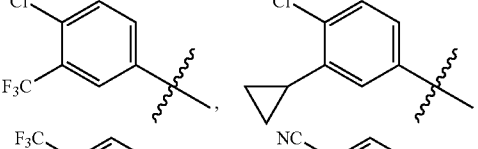
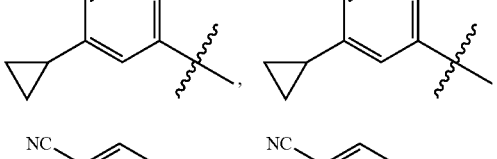
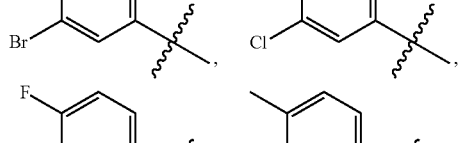
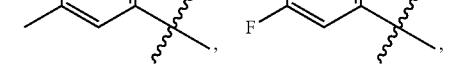

-continued

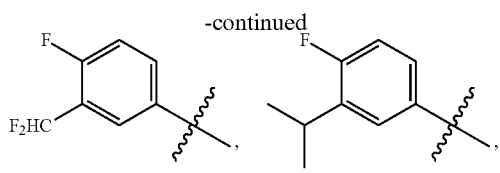

In certain embodiments, the present invention relates to compounds of Formula (VIa), Formula (VIIb), Formula (VIIc), or Formula (VId), and pharmaceutically acceptable salts thereof, wherein $R^5$ is an aryl or heteroaryl group derived from one of the following by removal of one hydrogen atom:

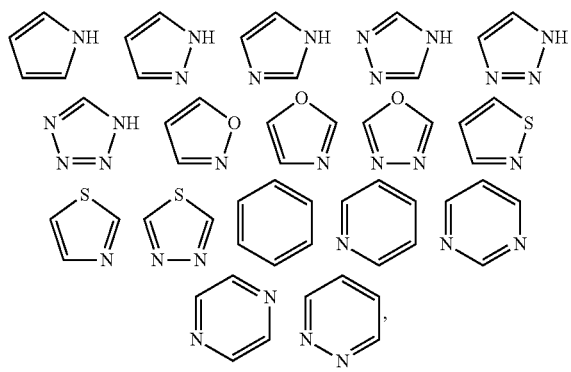

wherein each of the above shown groups is optionally substituted and is connected to the pyrazole or triazole ring through a carbon atom or, where possible, a nitrogen atom.

In certain embodiments, the present invention relates to compounds of any of the foregoing formulas, and pharmaceutically acceptable salts thereof, wherein $R^5$ is a heterocyclic group derived from one of the following by removal of one hydrogen atom:

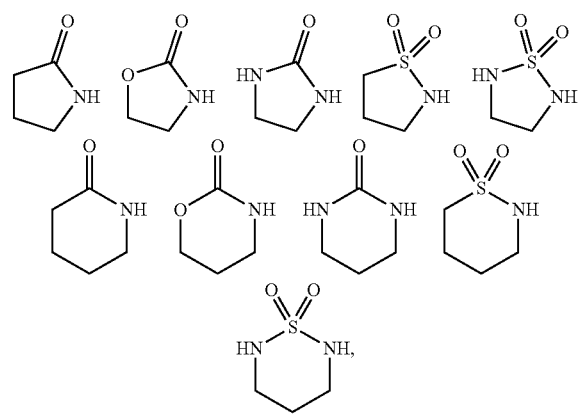

wherein each of the above shown groups is optionally substituted and is connected to the pyrazole or triazole ring through a carbon atom or a nitrogen atom. In certain embodiments, each of these groups is connected to the pyrazole or triazole ring through a nitrogen atom. In certain embodiments, each of these groups is substituted with one or more substituents independently selected from $C_1$-$C_6$-alkyl, aryl, heteroaryl, $C_3$-$C_6$-cycloalkyl, spiro-$C_1$-$C_6$-cycloalkyl and fused $C_1$-$C_6$-cycloalkyl.

In certain embodiments, the present invention relates to compounds of Formula (VIIa), Formula (VIIb), Formula (VIIc), or Formula (VIId), and pharmaceutically acceptable salts thereof, wherein $R^5$ is -L-$R^{12}$; wherein L is —O—, —N($R^{11}$)C(O)—, —OC(O)N($R^{11}$)—, —N($R^{11}$)C(O)O—, —N($R^{11}$)C(O)N($R^{11}$)—, or —N($R^{11}$)S(O)$_2$—; $R^{11}$ and $R^{12}$ are as previously defined.

In certain embodiments, the present invention relates to compounds of Formula (VIIa), Formula (VIIb), Formula (VIIc), or Formula (VIId), and pharmaceutically acceptable salts thereof, wherein

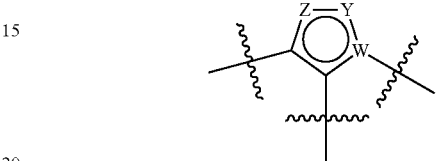

is selected from the groups below:

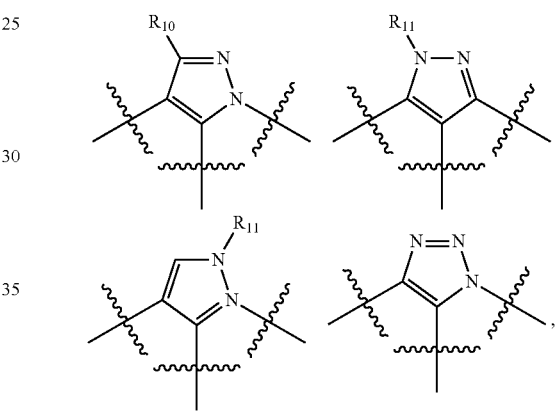

wherein $R^{10}$ and $R^{11}$ are as previously defined.

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In one aspect, the compounds of the invention are useful in HBV treatment by disrupting, accelerating, reducing, delaying and/or inhibiting normal viral core protein functions including, but not limited to, direct or indirect interaction with viral relaxed circular (rc) DNA, cccDNA, or reverse transcriptase, direct or indirect interaction with host proteins such as histones or host partners such as kinase, capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, the compounds of the invention disrupt and/or modulate the interaction between core protein and viral rcDNA, cccDNA or reverse transcriptase during vial infectivity. In yet another embodiment, the compounds of the invention disrupt and/or modulate the interaction between core protein and host partners or proteins during vial infectivity. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA. In another embodiment, the additional therapeutic agent is selected from immune modulator or immune stimulator therapies, which includes T-cell response activator AIC649 and biological agents belonging to the interferon class, such as interferon alpha 2a or 2b or modified interferons such as pegylated interferon, alpha 2a, alpha 2b, lamda; or STING (stimulator of interferon genes) modulator; or TLR modulators such as TLR-7 agonists, TLR-8 agonists or TLR-9 agonists; or therapeutic vaccines to stimulate an HBV-specific immune response such as virus-like particles composed of HBcAg and HBsAg, immune complexes of HBsAg and HBsAb, or recombinant proteins comprising HBx, HBsAg and HBcAg in the context of a yeast vector; or immunity activator such as SB-9200 of certain cellular viral RNA sensors such as RIG-I, NOD2, and MDA5 protein; or RNA interence (RNAi) or small interfering RNA (siRNA) such as ARC-520, ARC-521, ARB-1467, and ALN-HBV RNAi; or another core protein inhibitor or modulator; or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence such as REP 2139 and RG7834. In an embodiment of the combination therapy, the reverse transcriptase inhibitor is at least one of Zidovudine, Didanosine, Zalcitabine, ddA, Stavudine, Lamivudine, Aba-cavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-purin-9-yl)propyl][3-(4-morpholinyl) propyl] amino Imethyl)phenyl] acetate), GS-9620 (4-Amino-2-butoxy-8-[3-(1-pyrrolidinylmethyl)benzyl]-7, 8-dihydro-6(5H)-pteridinone), and RO6864018.

In another embodiment of the combination therapy, the TLR-8 agonist is GS-9688.

In an embodiment of these combination therapies, the compound and the additional therapeutic agent are co-formulated. In another embodiment, the compound and the additional therapeutic agent are co-administered.

In another embodiment of the combination therapy, administering the compound of the invention allows for administering of the additional therapeutic agent at a lower dose or frequency as compared to the administering of the at least one additional therapeutic agent alone that is required to achieve similar results in prophylactically treating an HBV infection in an individual in need thereof.

In another embodiment of the combination therapy, before administering the therapeutically effective amount of the compound of the invention, the individual is known to be refractory to a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In still another embodiment of the method, administering the compound of the invention reduces viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another embodiment, administering of the compound of the invention causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

It should be understood that the compounds encompassed by the present invention are those that are suitably stable for use as pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl" "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, deuterium, tritium, —F, —Cl, —Br, —I, —OH, $C_1$-$C_{12}$-alkyl; $C_2$-$C_{12}$-alkenyl, $C_2$-$C_{12}$-alkynyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O—heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$— aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH— heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$— $C_2$-$C_8$-alkynyl, —$NHCO_2$—$C_3$-$C_{12}$-cycloalkyl, —$NHCO_2$-aryl, —$NHCO_2$-heteroaryl, —$NHCO_2$— heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S) NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH) NH-aryl, —NHC(NH)NH-heteroaryl, —NHC(NH)NH-heterocycloalkyl, —NHC(NH)—$C_1$-$C_{12}$-alkyl, —NHC (NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH— heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; $NH_2$; $C_1$-$C_4$-alkylamino; di($C_1$-$C_4$-alkyl)amino; and $NO_2$. It is understood that the aryls, heteroaryls, alkyls, and the like can be further substituted. In some cases, each substituent in a substituted moiety is additionally optionally substituted when possible with one or more groups, each group being independently selected from $C_1$-$C_4$-alkyl; —$CF_3$, —$OCH_3$, —$OCF_3$, —F, —Cl, —Br, —I, —OH, —$NO_2$, —CN, and —$NH_2$. Preferably, a substituted alkyl group, such as a substituted methyl group, is substituted with one or more halogen atoms, more preferably one or more fluorine or chlorine atoms.

The term "halo" or "halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2*, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "amino acid" refers to naturally occurring and synthetic α, β, γ, or δ amino acids, and includes but is not limited to, amino acids found in proteins or intermediates in metabolism of amino acids or proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, citrulline, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from the group consisting of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl and β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NR$^u$-G(S$_c$)—C(O)-Q$^1$, wherein Q$^1$ is —SR$^v$, —NR$^v$R$^v$ or alkoxyl, R$^v$ is hydrogen or alkyl, S$_c$ is a side-chain of a naturally occurring or non-naturally occurring amino acid, G is C$_1$-C$_2$ alkyl, and R$^u$ is hydrogen; or R$^u$ and S$_c$ are taken together with the atoms to which they are attached to form a five-membered heterocyclic ring. In an embodiment, an amino acid derivative is provided as a substituent of a compound described herein, wherein the substituent is —O—C(O)-G(S$_c$)—NH-Q$^2$, wherein Q$^2$ is hydrogen or alkoxyl, S$_c$ is a side-chain of a naturally occurring or non-naturally occurring amino acid and G is C$_1$-C$_2$ alkyl. In certain embodiments, Q$^2$ and S$_c$ are taken together with the atoms to which they are attached to form a five-membered heterocyclic ring. In certain embodiments, G is an optionally substituted methylene and S$_c$ is selected from the group consisting of hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl and hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the invention will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, antileukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.
Combination and Alternation Therapy for HBV It has been recognized that drug-resistant variants of HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. The compounds can be used for combinations and are selected from the group consisting of a HBV polymerase inhibitor, interferon, TLR modulators such as TLR-7 agonists or TLR-9 agonists, therapeutic vaccines, immune activator of certain cellular viral RNA sensors, viral entry inhibitor, viral maturation inhibitor, distinct capsid assembly modulator, antiviral compounds of distinct or unknown mechanism, and combination thereof. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Preferred compounds for combination or alternation therapy for the treatment of HBV include 3TC, FTC, L-FMAU, interferon, adefovir dipivoxil, entecavir, telbivudine (L-dT), valtorcitabine (3'-valinyl L-dC), β-D-dioxolanyl-guanine (DXG), β-D-dioxolanyl-2,6-diaminopurine (DAPD), and β-D-dioxolanyl-6-chloropurine (ACP), famciclovir, penciclovir, lobucavir, ganciclovir, and ribavirin.

Although the invention has been described with respect to various preferred embodiments, it is not intended to be limited thereto, but rather those skilled in the art will recognize that variations and modifications may be made therein which are within the spirit of the invention and the scope of the appended claims.
Abbreviations Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; Boc$_2$O for di-tert-butyl-dicarbonate; Boc for t-butoxycarbonyl; Bpoc for 1-methyl-1-(4-biphenylyl)ethyl carbonyl; Bz for benzoyl; Bn for benzyl; BocNHOH for tert-butyl N-hydroxycarbamate; t-BuOK for potassium tert-butoxide; Bu$_3$SnH for tributyltin hydride; BOP for (benzotriazol-1-yloxy)tris(dimethylamino)phosphonium Hexafluorophosphate; Brine for sodium chloride solution in water; BSA for N,O-bis-(trimethylsilyl)acetamide; CDI for carbonyldiimidazole; CH$_2$Cl$_2$ and DCM for dichloromethane; CH$_3$ for methyl; CH$_3$CN for acetonitrile; Cs$_2$CO$_3$ for cesium carbonate; CuCl for copper (I) chloride; CuI for copper (I) iodide; dba for dibenzylidene acetone; dppb for diphenylphosphinobutane; DBU for 1,8-diazabicyclo[5.4.0]-undec-7-ene; DCC for N,N'-dicyclohexyl-carbodiimide; DEAD for diethylazodicarboxylate; DIAD for diisopropyl azodicarboxylate; DIPEA or (i-Pr)$_2$EtN for N,N,-diisopropylethyl amine; Dess-Martin periodinane for 1,1,1-tris(acetyloxy)-1,1-dihydro-1,2-benziodoxol-β-(1H)-one; DMAP for 4-dimethylamino-pyridine; DME for 1,2-dimethoxyethane; DMF for N,N-dimethylformamide; DMSO for dimethyl sulfoxide; DMT for di(p-methoxyphenyl)-phenylmethyl or dimethoxytrityl; DPPA for diphenylphosphoryl azide; EDC for N—(β-dimethylaminopropyl)-N'-ethylcarbodiimide; EDC HCl for N-(3-dimethylaminopropyl)-N'-ethylcarbodiimide hydrochloride; EtOAc for ethyl acetate; EtOH for ethanol; Et$_2$O for diethyl ether; HATU for O-(7-azabenzotriazol-1-yl)-N,N,N',N',-tetramethyluronium Hexafluoro-phosphate; HCl for hydrogen chloride; HOBT for 1-hydroxybenzotriazole; K$_2$CO$_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethyl-piperidinate; MeOH for methanol; Mg for magnesium; MOM for methoxymethyl; Ms for mesyl or $-SO_2-CH_3$; $Ms_2O$ for methanesulfonic anhydride or mesyl-anhydride; MTBE for t-butyl methyl ether; $NaN(TMS)_2$ for sodium bis(trimethylsilyl)amide; NaCl for sodium chloride; NaH for sodium hydride; $NaHCO_3$ for sodium bicarbonate or sodium hydrogen carbonate; $Na_2CO_3$ for sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4HCO_3$ for ammonium bicarbonate; $NH_4C_1$ for ammonium chloride; NMO for N-methyl-morpholine N-oxide; $NaIO_4$ for sodium periodate; Ni for nickel; NSFI for N-fluorobenzene-sulfonimide; OH for hydroxyl; o/n for overnight; $OsO_4$ for osmium tetroxide; PTSA for p-toluenesulfonic acid; PPTS for pyridinium p-toluenesulfonate; TBAF for tetrabutyl-ammonium fluoride; TEA or $Et_3N$ for triethylamine; TES for triethylsilyl; TESCl for triethylsilyl chloride; TESOTf for triethylsilyl trifluoro-methanesulfonate; TFA for trifluoroacetic acid; THF for tetrahydro-furan; TMEDA for N,N,N',N'-tetramethylethylene-diamine; TPP or $PPh_3$ for triphenyl-phosphine; Troc for 2,2,2-trichloroethyl carbonyl; Ts for tosyl or $-SO_2-C_6H_4CH_3$; $Ts_2O$ for tolylsulfonic anhydride or tosyl-anhydride; TsOH for p-tolylsulfonic acid; Pd for palladium; Ph for phenyl; POPd for dihydrogen dichlorobis(di-tert-butylphosphinito-κP)palladate(II); $Pd_2(dba)_3$ for tris(dibenzylideneacetone) dipalladium (0); $Pd(PPh_3)_4$ for tetrakis(triphenyl-phosphine)palladium (0); $PdCl_2(PPh_3)_2$ for trans-dichlorobis-(triphenylphosphine)palladium (II); Pt for platinum; Rh for rhodium; rt for room temperature; Ru for ruthenium; SFC for supercritical fluid chromatography; TBS for tert-butyl dimethylsilyl; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis. Certain reactions can be conducted as generally described in WO 2017/011160, WO 2017/011162, and WO 2017/011163.

The compounds of Formula I may be prepared via several different synthetic routes from a variety of optionally substituted phenyl, heteroaryl, or fused bicyclic aryl or heteroaryl precursors using the chemical transformations that are known to those skilled in the art. A general synthetic strategy is shown in Scheme 1. For example an intermediate 1-1 where X is a leaving group, such as a halogen, and Pg is a protecting group, such as Boc or benzyl, can be coupled to a nucleophile 1-2. The nature of the coupling depends on the identity of $R^5$. For example if $R^5$ is aryl or heteroaryl, then Q could be boron, tin, or zinc and the reaction could be catalyzed by palladium to give the desired product 1-3. Alternatively, if $R^5$ is a nucleophilic nitrogen and Q could be hydrogen, then copper catalyzed compling would give intermediate 1-3. To continue the reaction sequence the Pg would be removed from intermediate 1-3 followed by coupling with electrophile 1-4 where Lg is a leaving group, such as phenol, to give desired compound 1-5.

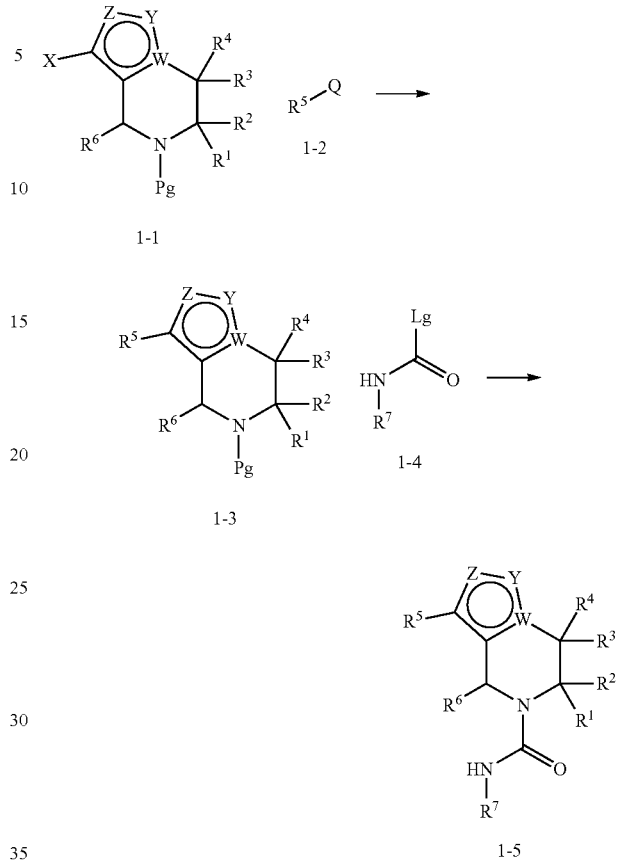

Alternatively, as shown in Scheme 2, intermediate 2-1, could react with electrophile 2-2, to give intermediate 2-3. Coupling between intermediate 2-3 and nucleophile 2-4 would give desired compound 2-5.

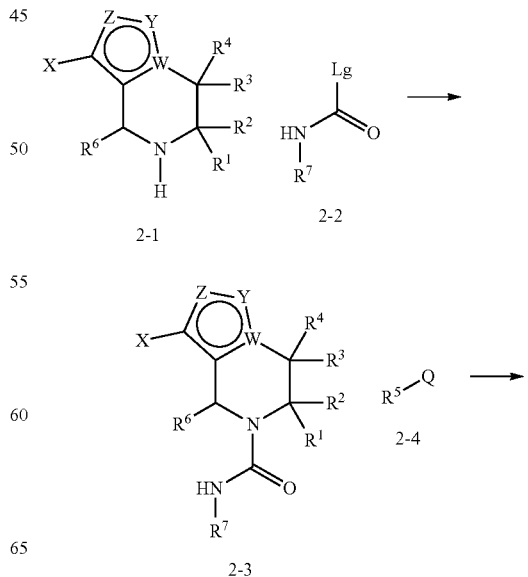

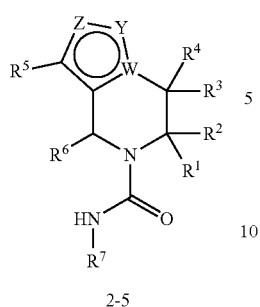

2-5

As shown in Scheme 3, an intermediate 3-5 corresponding to related intermediates shown above could be synthesized as follows. Reductive amination between amine 3-1 and aldehyde 3-2 followed by treatment with boc anhydride, would give with boc-protected amine 3-3. Formation of the mesylate with MsCl followed by treatment with a strong base such as sodium hydride would give intermediate 3-4, which upon treatment with an electrophilic halogen source such as NBS or NIS would give intermediate 3-5, where X is bromine or iodine respectively.

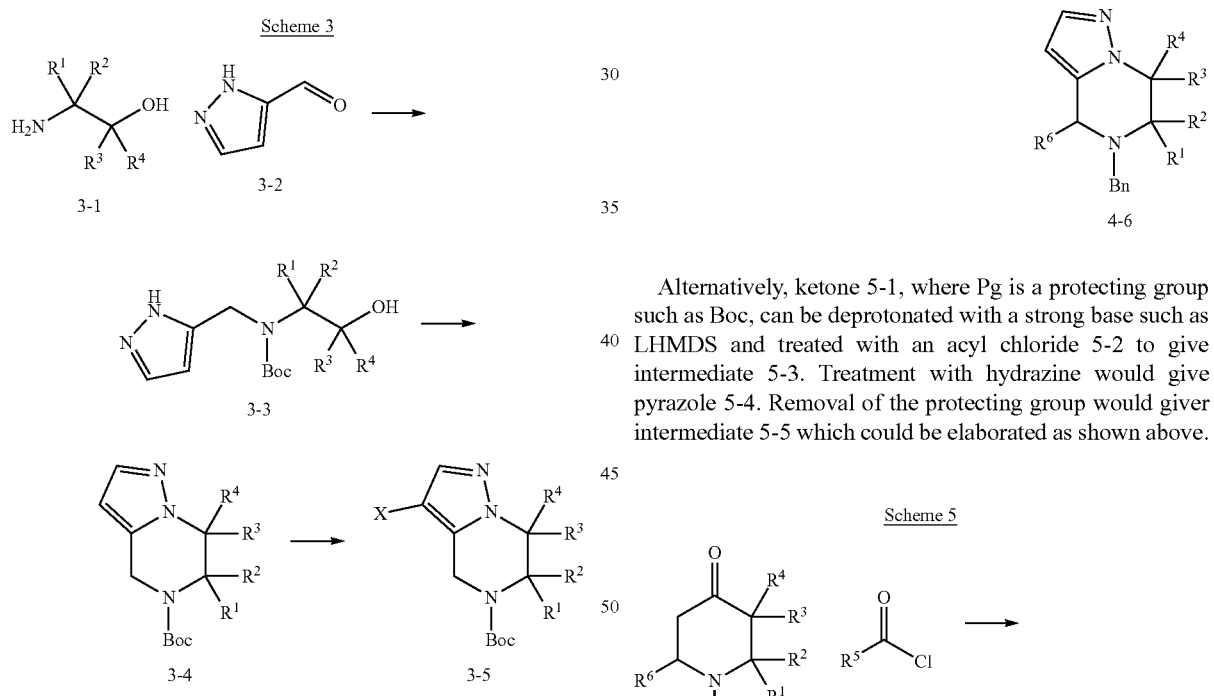

Alternatively, diol 4-1 could be activated with thionyl chloride then oxidized with RuCl3 and sodium periodate to give compound 4-2. Nucleophilic displacement with pyrazole under basic conditions could give intermediate 4-3. Conversion of the alcohol could occur via Mitsunobu reaction with phthalamide, followed by liberation of the free amine with hydrazine and protection as the benzyl amine via reductive amination with benzaldehyde to give intermediate 4-4. Condensation with aldehyde 4-5 under acidic conditions could give intermediate 4-6 which could be utilized as above.

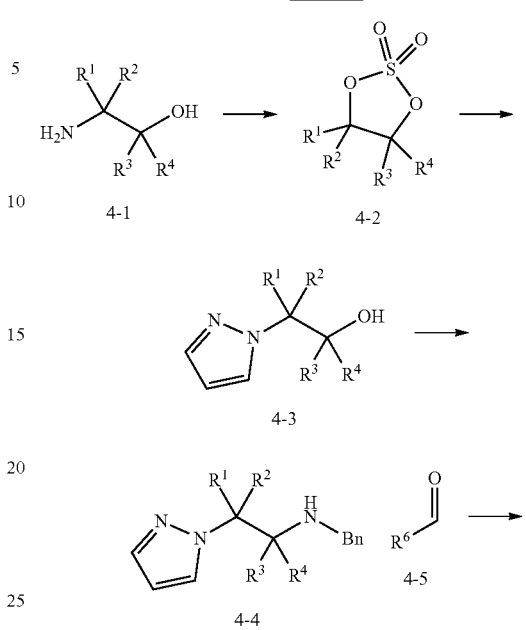

Alternatively, ketone 5-1, where Pg is a protecting group such as Boc, can be deprotonated with a strong base such as LHMDS and treated with an acyl chloride 5-2 to give intermediate 5-3. Treatment with hydrazine would give pyrazole 5-4. Removal of the protecting group would giver intermediate 5-5 which could be elaborated as shown above.

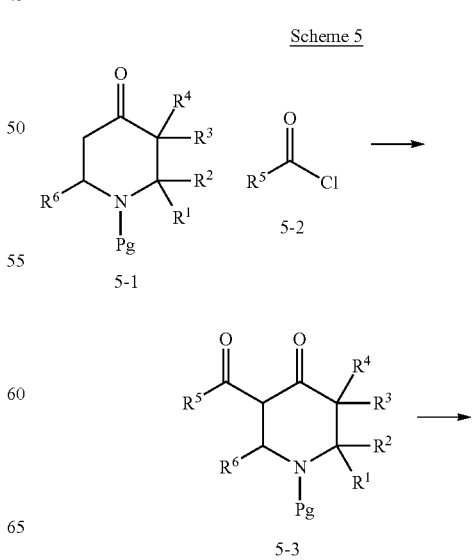

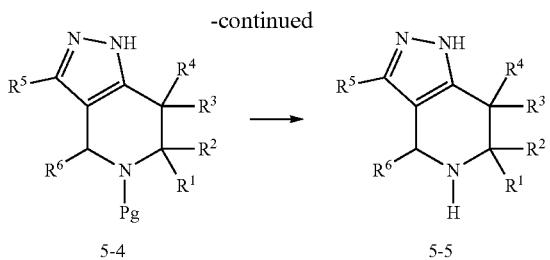

5-4    5-5

As shown in Scheme 6, an intermediate 6-5 corresponding to related intermediates shown above could be synthesized as follows. Reductive amination between amine 6-1 and benzaldehyde followed by alkylation with propargyl bromide would give amine 6-2. Treatment of alcohol 6-2 with thionyl chloride would give alkyl chloride 6-3. Addition of sodium azide at elevated temperature would give an azide intermediate that could with would then undergo [3+2] cycloaddition to give triazole 6-4, which upon treatment with an electrophilic halogen source such as NBS or NIS would give intermediate 6-5, where X is bromine or iodine respectively.

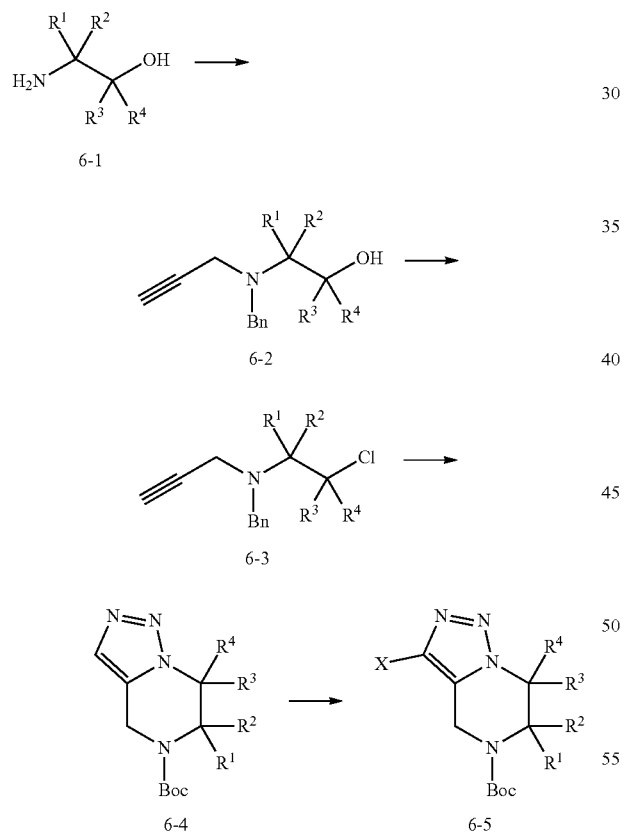

It will be appreciated that, with appropriate manipulation and protection of any chemical functionality, synthesis of compounds of Formula I is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

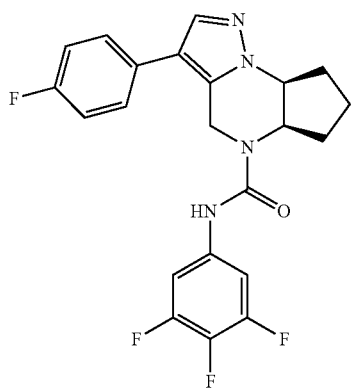 [SMILES: O=C(Nc1cc(F)c(F)c(F)c1)N1Cc2c(-c3ccc(F)cc3)cnn2[C@H]2CCC[C@H]21]

Step 1a.

A suspension of (1R,2R)-2-aminocyclopentan-1-ol hydrochloride (1.718 g, 12.49 mmol) and 1H-pyrazole-5-carbaldehyde (1 g, 10.41 mmol), and sodium bicarbonate (1.049 g, 12.49 mmol) in MeOH (52.0 ml) was stirred for 1 h. The reaction mixture was cooled to 0° C. followed by addition of sodium borohydride (0.472 g, 12.49 mmol). The reaction was stirred for 30 minutes followed by careful addition of water (52.0 ml) and Boc-anhydride (2.90 ml, 12.49 mmol). The reaction was stirred for 18 h. The reaction mixture was concentrated under vaccum. The reaction mixture was diluted with EtOAc and washed with brine. The organic layer was dried with $Na_2SO_4$, filtered and concentrated. The crude product chromatographed (silica, methanol/dichloromethane) to give the desired compound (0.78 g, 2.77 mmol, 27% yield) as a yellow oil that crystalized upon standing.

Step 1b.

To a suspension of the compound from step 1a (0.78 g, 2.77 mmol) and Et$_3$N (1.16 mL, 8.32 mmol) in DCM (7.8 mL) at 0° C. was added mesyl chloride (0.324 mL, 4.16 mmol). The reaction mixture was warmed to rt and stirred for 1 h. The reaction was extracted with DCM, washed with water and brine. The organic layer was dried (Na$_2$SO$_4$), filtered and concentrated. The desired product was used without further purification (0.95 g, 96%).

Step 1c.

To a solution of compound from step 1b (0.95 g, 2.65 mmol) in DMF (8.8 mL) at 0° C. was added sodium hydride (127 mg, 3.18 mmol, 60%). The reaction mixture was warmed to rt and stirred for 18 h. The reaction mixture was diluted with EtOAc then washed with sat. NH$_4$C$_1$, water, and brine. The organic layer was dried with Na$_2$SO$_4$, filtered and concentrated. The crude product chromatographed (silica, methanol/dichloromethane) to give the desired compound (280 mg, 1.063 mmol, 40% yield).

Step 1d.

To a solution of compound from step 1c (280 mg, 1.063 mmol) in acetonitrile (3.5 mL) was added N-iodosuccinimide (359 mg, 1.595 mmol). The reaction mixture was stirred for 1 h. The reaction mixture was diluted with EtOAc then washed with sat. aqueous Na$_2$S$_2$O$_3$, water, and brine. The organic layer was dried with Na$_2$SO$_4$, filtered and concentrated. The crude product chromatographed (silica, methanol/dichloromethane) to give the desired compound (380 mg, 0.976 mmol, 92% yield).

Step 1e.

To a solution of compound from step 1d (190 mg, 0.488 mmol) and (4-fluorophenyl)boronic acid (102 mg, 0.732) in dioxane (1.3 mL) and water (0.3 mL) was added K$_2$CO$_3$ (202 mg, 1.464 mmol) and Pd(PPh$_3$)$_4$ (28 mg, 0.024 mmol). The reaction mixture was stirred at 80° C. for 18 h. The reaction mixture was diluted with EtOAc then washed with sat. aqueous Na$_2$S$_2$O$_3$, water, and brine. The organic layer was dried with Na$_2$SO$_4$, filtered and concentrated. The crude product chromatographed (silica, methanol/dichloromethane) to give the desired compound (170 mg, 0.476 mmol, 97% yield).

Step 1f.

To a solution of compound from step 1e (170 mg, 0.476 mmol) in DCM (2 mL) was added TFA (0.5 mL, 6.49 mmol). The reaction mixture was stirred at rt for 3 h then concentrated under vacuum. The desired product was used without further purification.

Step 1g.

A solution of compound from step 1f (40 mg, 0.155 mmol), Et$_3$N (60 µL, 0.466 mmol) and phenyl (3,4,5-trifluorophenyl)carbamate (50 mg, 0.187 mmol) in DMF (1.5 mL) was stirred for 1 h. The crude reaction mixture was purified via prep-HPLC (C18, acetonitrile/water) to give the title compound (6 mg, 9%). ESI-MS m/z=429.13, 430.14 [M–H]$^-$.

Example 2

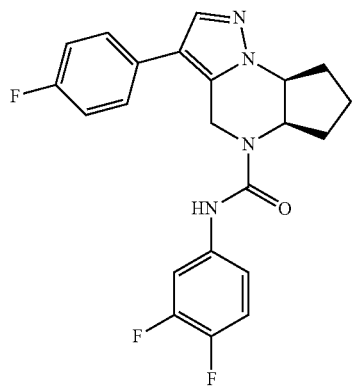 [SMILES: O=C(Nc1ccc(F)c(F)c1)N1Cc2c(-c3ccc(F)cc3)cnn2[C@H]2CCC[C@H]21]

A solution of compound from step 1f (40 mg, 0.155 mmol), Et$_3$N (60 µL, 0.466 mmol) and phenyl (3,4-difluorophenyl)carbamate (50 mg, 0.187 mmol) in DMF (1.5 mL) was stirred for 1 h. The crude reaction mixture was purified via prep-HPLC (C18, acetonitrile/water) to give the title compound (10 mg, 16%). ESI-MS m/z=411.14 [M–H]$^-$.

Example 3

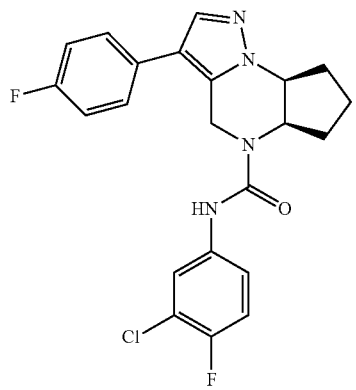 [SMILES: O=C(Nc1ccc(F)c(Cl)c1)N1Cc2c(-c3ccc(F)cc3)cnn2[C@H]2CCC[C@H]21]

A solution of compound from step 1f (40 mg, 0.155 mmol), Et$_3$N (60 µL, 0.466 mmol) and phenyl (3-chloro-4-fluorophenyl)carbamate (50 mg, 0.187 mmol) in DMF (1.5 mL) was stirred for 1 h. The crude reaction mixture was purified via prep-HPLC (C18, acetonitrile/water) to give the title compound (8 mg, 12%). ESI-MS m/z=427.11, 429.11 [M–H]$^-$.

Example 4

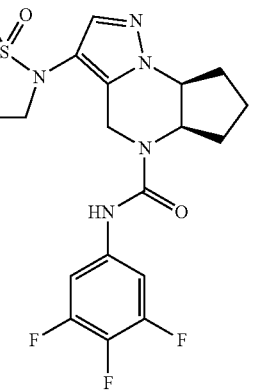

Step 4a.

To a suspension of compound from step 1d (190 mg, 0.488 mmol), K₂CO₃ (202 mg, 1.464 mmol), and CuI (18.6 mg, 0.098 mmol) in DMSO (1.6 mL) was added trans-N,N'-dimethylcyclohexane-1,2-diamine (15 µL, 0.098 mmol) and isothiazolidinone 1,1-dioxide (67 µL, 0.732 mmol). The reaction mixture was stirred at 80° C. for 18 h. The reaction mixture was diluted with EtOAc then washed with sat. aqueous Na₂S₂O₃, water, and brine. The organic layer was dried with Na₂SO₄, filtered and concentrated. The crude product chromatographed (silica, methanol/dichloromethane) to give the desired compound (115 mg, 0.301 mmol, 62% yield).

Step 4b.

To a solution of compound from step 4a (115 mg, 0.301 mmol) in DCM (2 mL) was added TFA (0.5 mL, 6.49 mmol). The reaction mixture was stirred at rt for 3 h then concentrated under vacuum. The desired product was used without further purification.

Step 4c.

A solution of compound from step 4b (30 mg, 0.106 mmol), Et₃N (44 µL, 0.127 mmol) and phenyl (3,4,5-trifluorophenyl)carbamate (32 mg, 0.127 mmol) in DMF (1.5 mL) was stirred for 1 h. The crude reaction mixture was purified via prep-HPLC (C18, acetonitrile/water) to give the title compound (9 mg, 19%). ESI-MS m/z=454.12[M−H]⁻.

Example 13

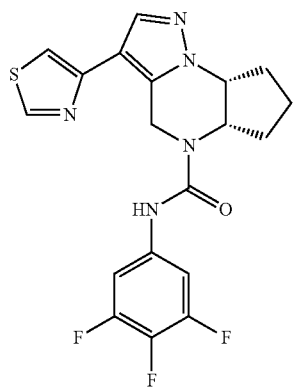 [SMILES: O=C(Nc1cc(F)c(F)c(F)c1)N1Cc2c(-c3cscn3)cnn2[C@@H]2CCC[C@@H]21]

Step 13a.

The desired compound was prepared from the compound of example 1 following a procedure similar to that described in steps 1a-1d, ESI-MS m/z=390.08 [M+H]⁺.

Step 13b.

To a mixture of compound from step 13a (63 mg, 0.162 mmol), thiazol-4-ylboronic acid (20.87 mg, 0.162 mmol), K₂CO₃ (67.1 mg, 0.486 mmol) in dioxane (2 mL) and water (0.4 mL) was added Pd(PPh₃)₄ (21 mg, 0.018 mmol) under N₂. The mixture was stirred at 80° C. for 15 h. The reaction mixture was diluted with EtOAc then washed with sat. aqueous Na₂S₂O₃, water, and brine. The organic layer was dried with Na₂SO₄, filtered and concentrated. The crude product chromatographed (silica, methanol/dichloromethane) to give the desired compound (40.0 mg, 71%).

Step 13c.

To a solution of compound from step 13b (70 mg, 0.202 mmol) in DCM (2 mL) was added TFA (0.08 mL, 1.01 mmol). The reaction mixture was stirred at rt for 2 h then concentrated under vacuum. The desired product was used without further purification.

Step 13d.

A solution of compound from step 13c (24 mg, 0.097 mmol), Et₃N (41 µL, 0.292 mmol) and phenyl (3,4,5-trifluorophenyl)carbamate (26 mg, 0.097 mmol) in DMF (2 mL) was stirred for 10 h. The crude reaction mixture was purified via prep-HPLC (C18, acetonitrile/water) to give the title compound (6.2 mg, 15%). ESI-MS m/z=420.29 [M+H]⁺.

Example 14

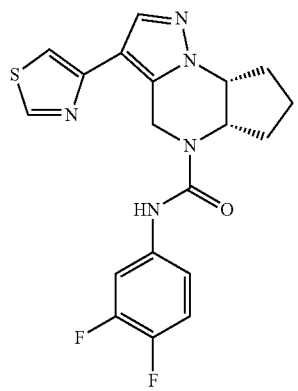 [SMILES: O=C(Nc1ccc(F)c(F)c1)N1Cc2c(-c3cscn3)cnn2[C@@H]2CCC[C@@H]21]

A solution of compound from step 13a (24 mg, 0.097 mmol), Et₃N (41 µL, 0.292 mmol) and phenyl (3,4-difluorophenyl)carbamate (24.3 mg, 0.097 mmol) in DMF (2 mL) was stirred for 10 h. The crude reaction mixture was purified via prep-HPLC (C18, acetonitrile/water) to give the title compound (6.5 mg, 17%). ESI-MS m/z=402.29 [M+H]⁺.

Example 15

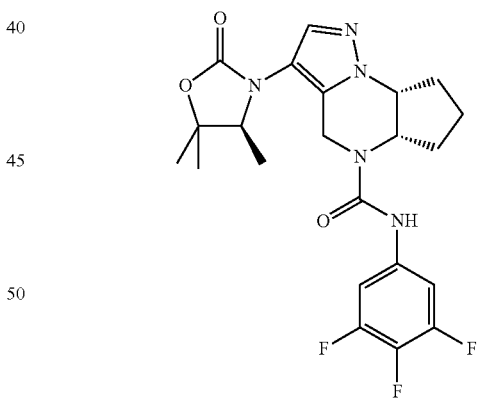

Step 15a.

To a suspension of compound from step 13a (270 mg, 0.694 mmol), K₃PO₄ (14.72 mg, 0.069 mmol), and CuI (13.2 mg, 0.069 mmol) in dioxane (3 mL) was added trans-N,N'-dimethylcyclohexane-1,2-diamine (10.9 µL, 0.069 mmol) and (S)-4,5,5-trimethyloxazolidin-2-one (90 mg, 0.694 mmol). The reaction mixture was stirred at 100° C. for 16 h. The reaction mixture was diluted with EtOAc then washed with sat. aqueous Na₂S₂O₃, water, and brine. The organic layer was dried with Na₂SO₄, filtered and concentrated. The crude product chromatographed (silica, methanol/dichloromethane) to give the desired compound (100 mg, 37%).

47

Step 15b.

To a solution of compound from step 15a (100 mg, 0.256 mmol) in DCM (2 mL) was added TFA (59 µL, 0.768 mmol). The reaction mixture was stirred at rt for 3 h then concentrated under vacuum. The desired product was used without further purification.

Step 15c.

A solution of compound from step 15b (24.5 mg, 0.084 mmol), Et$_3$N (35 µL, 0.253 mmol) and phenyl (3,4,5-trifluorophenyl)carbamate (22.6 mg, 0.084 mmol) in DMF (2 mL) was stirred for 6 h. The crude reaction mixture was purified via prep-HPLC (C18, acetonitrile/water) to give the title compound (15 mg, 38%). ESI-MS m/z=464.20 [M+H]$^+$.

Example 16

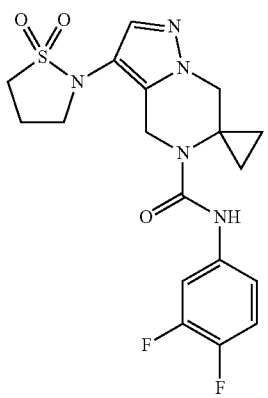 [SMILES: O=C(Nc1ccc(F)c(F)c1)N1Cc2c(N3CCCS3(=O)=O)cnn2CC12CC2]

Step 16a.

Into a suspension of (1-aminocyclopropyl)methanol hydrochloride (0.371 g, 3.0 mmol), 1H-pyrazole-5-carbaldehyde (0.241 g, 2.5 mmol) and MgSO4 (2.2 g, 18 mmol) in CH$_2$Cl$_2$ (5.0 ml), trimethylamine (0.84 mL, 6.0 mmol) was added at rt and stirred o/n. The solid was collected under vacuum and washed with CH$_2$Cl$_2$ (10.0 ml). The collected solid was suspended in EtOH (6 mL) and MeOH (3 mL), and cooled to 0° C. followed by addition of sodium borohydride (60% w/w, 0.16 g, 2.5 mmol). The reaction was stirred for one hour followed by careful addition of water (5.0 ml), then Boc$_2$O (0.66 g, 3 mmol). It was stirred ar rt o/n and concentrated. The mixture was diluted with EtOAc and washed with brine. The organic layer was dried (Na$_2$SO$_4$), filtered and concentrated. The crude was chromatographed (silica, methanol/dichloromethane) to give the desired compound (0.32 g, 50% yield) as a yellow oil. $^1$HNMR (CDCl$_3$, ppm): 7.53 (brs, 1H), 6.24 (brs, 1H), 4.47 (brs, 2H), 3.65-3.51 (brd, 2H), 1.48-1.28 (brd, 9H), 0.96 (brs, 4H).

Step 16b.

The title compound was prepared using procedures similar to those described above; ESI-MS m/z=424.30 [M+H]$^+$. The following examples were prepared using procedures similar to those described above:

| Example | Structure | ESIMS (M − H)$^-$ or (M + H)$^+$ |
|---|---|---|
| 5 | 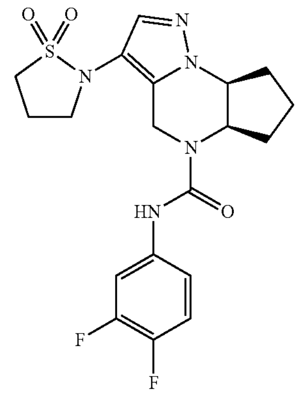 | 463.13 [M − H]$^-$ |
| 6 | 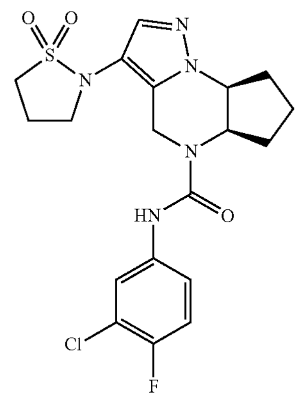 | 452.10, 454.10 [M − H]$^-$ |
| 7 | 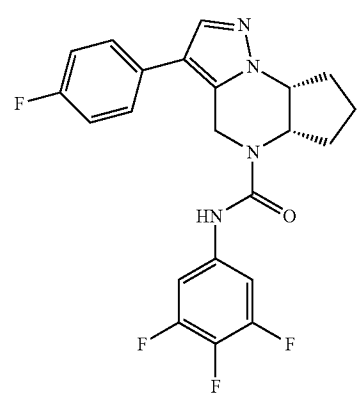 [SMILES: O=C(Nc1cc(F)c(F)c(F)c1)N1Cc2c(-c3ccc(F)cc3)cnn2[C@@H]2CCC[C@@H]21] | 431.16 [M + H]$^+$ |
| 8 | 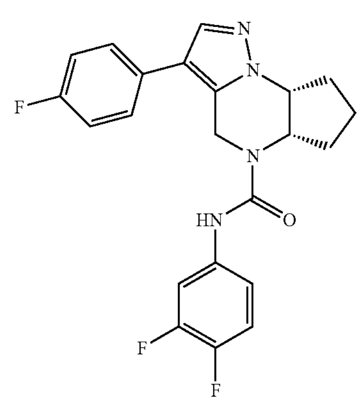 [SMILES: O=C(Nc1ccc(F)c(F)c1)N1Cc2c(-c3ccc(F)cc3)cnn2[C@@H]2CCC[C@@H]21] | 413.17 [M + H]$^+$ |

-continued

| Example | Structure | ESIMS (M − H)⁻ or (M + H)⁺ |
|---|---|---|
| 9 | (3-(4-fluorophenyl)pyrazolo-fused cyclopentane urea with 3-chloro-4-fluorophenyl) | 429.14, 431.14 [M + H]⁺ |
| 10 | (isothiazolidine 1,1-dioxide pyrazolo-fused cyclopentane urea with 3,4,5-trifluorophenyl) | 456.14 [M + H]⁺ |
| 11 | (isothiazolidine 1,1-dioxide pyrazolo-fused cyclopentane urea with 3,4-difluorophenyl) | 438.33 [M + H]⁺ |

| Example | Structure | ESIMS (M − H)⁻ or (M + H)⁺ |
|---|---|---|
| 12 | (isothiazolidine 1,1-dioxide pyrazolo-fused cyclopentane urea with 3-chloro-4-fluorophenyl) | 454.30, 456.30 [M + H]⁺ |
| 17 | (5,5-dimethyl-4-methyl-oxazolidin-2-one pyrazolo-fused cyclopentane urea with 3,4-difluorophenyl) | 446.21 [M + H]⁺ |
| 18 | (5,5-dimethyl-4-methyl-oxazolidin-2-one pyrazolo-fused cyclopentane urea with 3-chloro-4-fluorophenyl) | 462.18, 464.18 [M + H]⁺ |

-continued
| Example | Structure | ESIMS (M − H)⁻ or (M + H)⁺ |
|---|---|---|
| 19 | 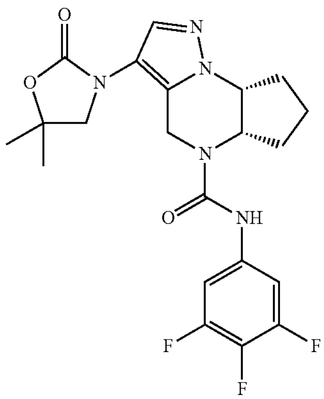 [SMILES: CC1(C)CN(c2cnn3c2CN(C(=O)Nc2cc(F)c(F)c(F)c2)[C@H]2CCC[C@H]23)C(=O)O1] | 450.25 [M + H]⁺ |
| 26 | 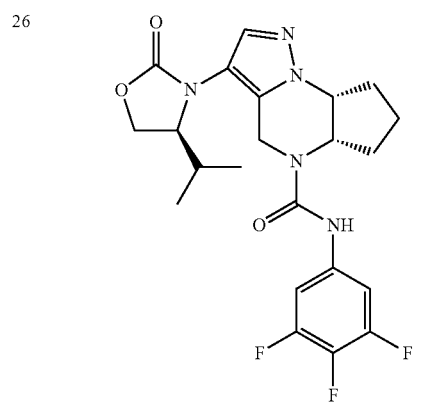 | 464.30 [M + H]⁺ |
| 36 | 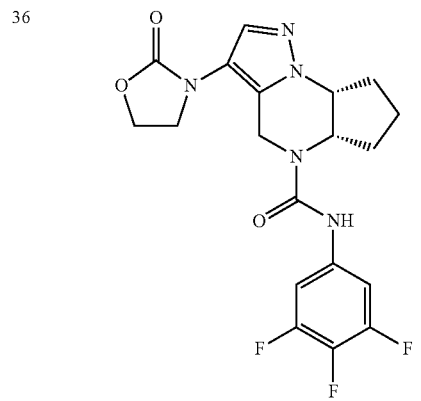 | 422.10 [M + H]⁺ |
-continued
| Example | Structure | ESIMS (M − H)⁻ or (M + H)⁺ |
|---|---|---|
| 37 | 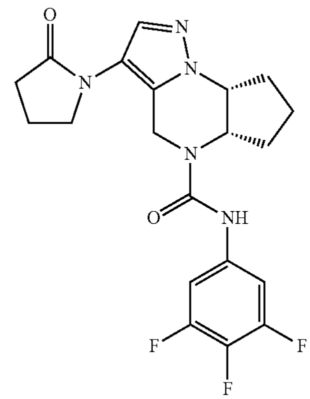 [SMILES: O=C1CCCN1c1cnn2c1CN(C(=O)Nc1cc(F)c(F)c(F)c1)[C@H]1CCC[C@H]12] | 420.20 [M + H]⁺ |
| 38 | 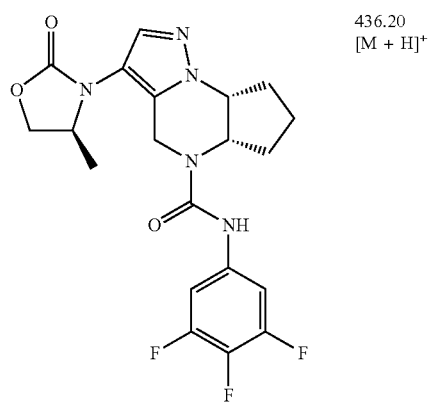 | 436.20 [M + H]⁺ |
| 39 | 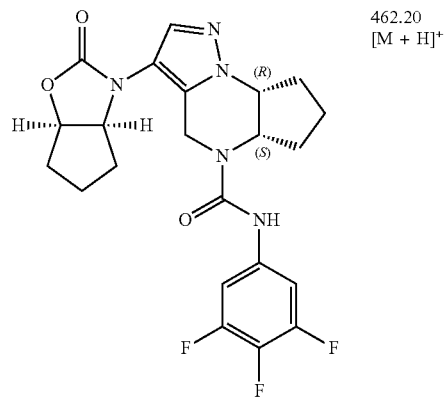 | 462.20 [M + H]⁺ |

TABLE 53-continued
| Example | Structure | ESIMS (M − H)⁻ or (M + H)⁺ |
|---|---|---|
| 40 | 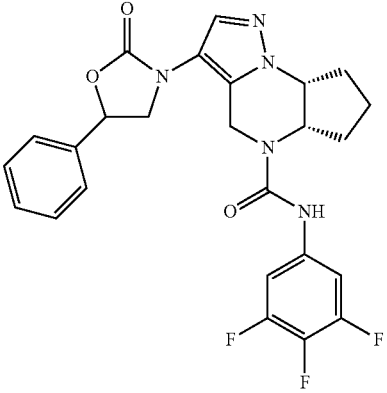 [SMILES: O=C1OC(c2ccccc2)CN1c1cnn2c1CN(C(=O)Nc1cc(F)c(F)c(F)c1)[C@H]1CCC[C@H]12] | 498.20 [M + H]⁺ |
| 41 | 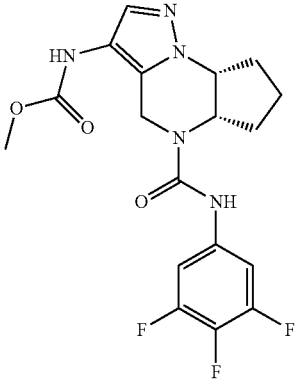 [SMILES: COC(=O)Nc1cnn2c1CN(C(=O)Nc1cc(F)c(F)c(F)c1)[C@H]1CCC[C@H]12] | 410.15 [M + H]⁺ |
| 42 | 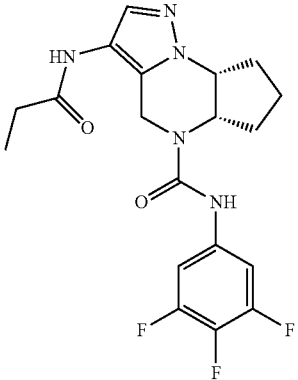 | 418.15 [M + H]⁺ |
TABLE 54-continued
| Example | Structure | ESIMS (M − H)⁻ or (M + H)⁺ |
|---|---|---|
| 43 | 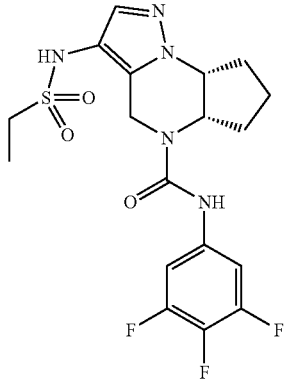 [SMILES: CCS(=O)(=O)Nc1cnn2c1CN(C(=O)Nc1cc(F)c(F)c(F)c1)[C@H]1CCC[C@H]12] | 444.15 [M + H]⁺ |
| 44 | 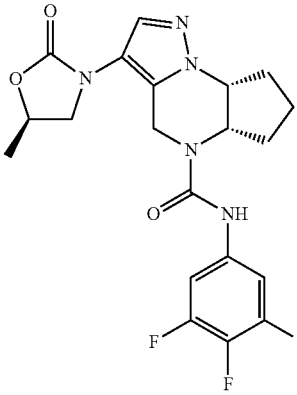 | 436.30 [M + H]⁺ |
| 45 | 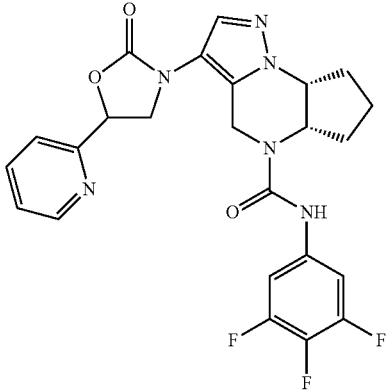 | 499.25 [M + H]⁺ |

| Example | Structure | ESIMS (M − H)⁻ or (M + H)⁺ |
|---|---|---|
| 46 | 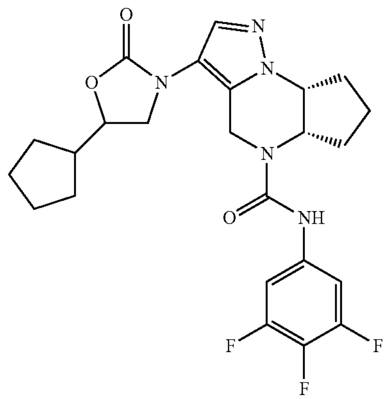 [SMILES: O=C1OC(C2CCCC2)CN1c1cnn2c1CN(C(=O)Nc1cc(F)c(F)c(F)c1)[C@H]1CCC[C@H]12] | 490.30 [M + H]⁺ |
| 47 | 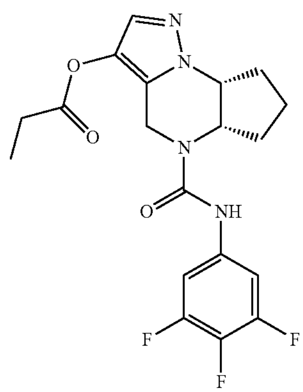 [SMILES: CCC(=O)Oc1cnn2c1CN(C(=O)Nc1cc(F)c(F)c(F)c1)[C@H]1CCC[C@H]12] | 409.15 [M + H]⁺ |
| 48 | 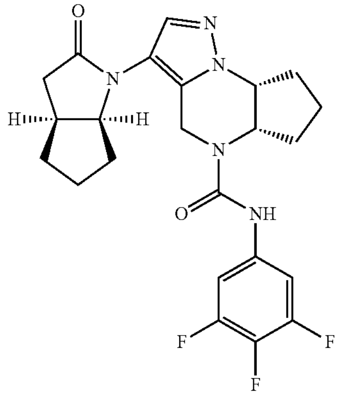 [SMILES: O=C(Nc1cc(F)c(F)c(F)c1)N1Cc2c(N3C(=O)C[C@@H]4CCC[C@@H]43)cnn2[C@@H]2CCC[C@@H]21] | 460.30 [M + H]⁺ |
| 49 | | 460.30 [M + H]⁺ |
| 50 | | 446.25 [M + H]⁺ |
| 51 | | 470.25 [M + H]⁺ |

| Example | Structure | ESIMS (M − H)⁻ or (M + H)⁺ |
|---|---|---|
| 52 | 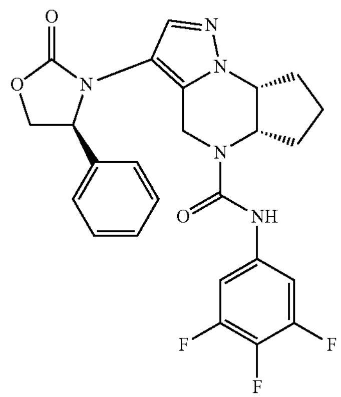 [SMILES: O=C(Nc1cc(F)c(F)c(F)c1)N1Cc2c(N3C(=O)OC[C@@H]3c3ccccc3)cnn2[C@@H]2CCC[C@@H]21] | 498.25 [M + H]⁺ |
| 53 | 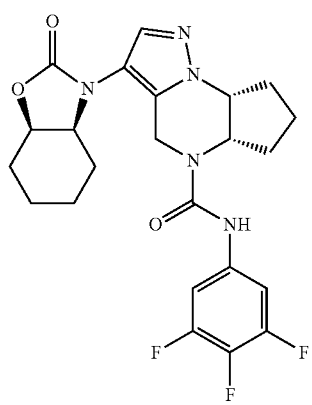 [SMILES: O=C(Nc1cc(F)c(F)c(F)c1)N1Cc2c(N3C(=O)O[C@@H]4CCCC[C@@H]43)cnn2[C@@H]2CCC[C@@H]21] | 476.25 [M + H]⁺ |
| 54 | 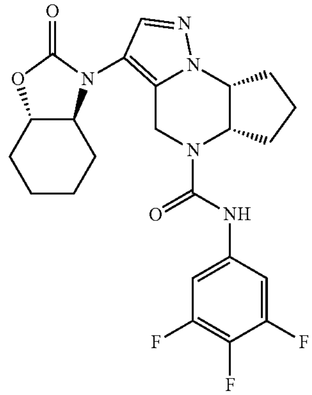 [SMILES: O=C(Nc1cc(F)c(F)c(F)c1)N1Cc2c(N3C(=O)O[C@H]4CCCC[C@@H]43)cnn2[C@@H]2CCC[C@@H]21] | 476.25 [M + H]⁺ |
| 55 | | 448.20 [M + H]⁺ |
| 56 | | 490.30 [M + H]⁺ |
| 57 | | 476.25 [M + H]⁺ |

TABLE-continued
| Example | Structure | ESIMS (M − H)⁻ or (M + H)⁺ |
|---|---|---|
| 58 | 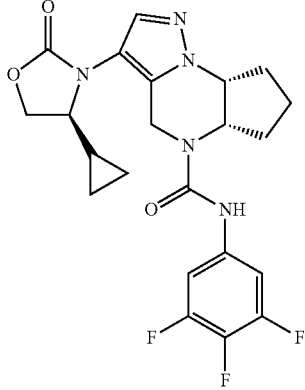 [SMILES: O=C(Nc1cc(F)c(F)c(F)c1)N1Cc2c(N3C(=O)OC[C@@H]3C3CC3)cnn2[C@@H]2CCC[C@@H]21] | 462.15 [M + H]⁺ |
| 59 | 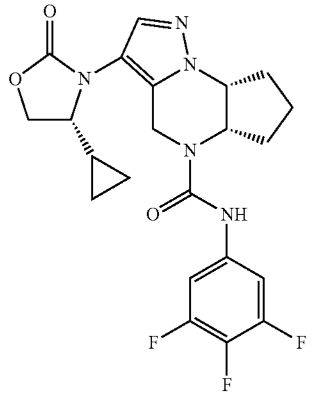 [SMILES: O=C(Nc1cc(F)c(F)c(F)c1)N1Cc2c(N3C(=O)OC[C@H]3C3CC3)cnn2[C@@H]2CCC[C@@H]21] | 462.15 [M + H]⁺ |
| 60 | 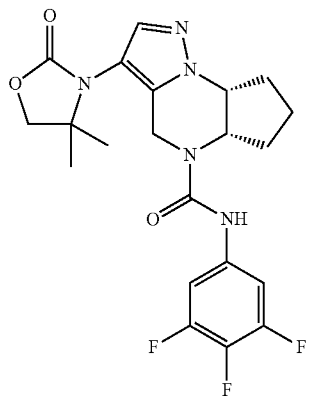 [SMILES: CC1(C)COC(=O)N1c1cnn2c1CN(C(=O)Nc1cc(F)c(F)c(F)c1)[C@H]1CCC[C@H]12] | 450.30 [M + H]⁺ |
| 61 | 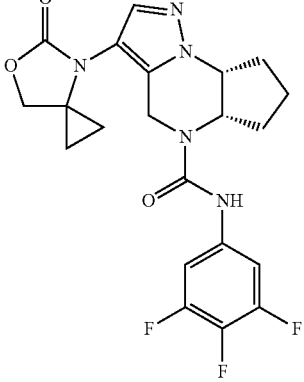 | 448.25 [M + H]⁺ |
| 62 | | 458.15 [M + H]⁺ |
| 63 | | 458.00 [M + H]⁺ |

| Example | Structure | ESIMS (M − H)− or (M + H)+ |
|---|---|---|
| 64 | 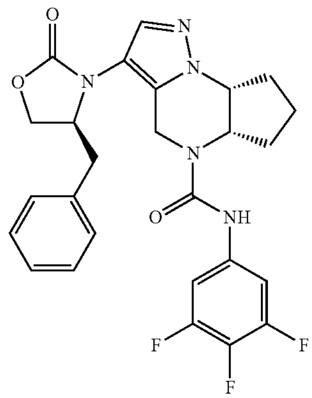 [SMILES: O=C(Nc1cc(F)c(F)c(F)c1)N1Cc2c(N3C(=O)OC[C@@H]3Cc3ccccc3)cnn2[C@@H]2CCC[C@@H]21] | 512.25 [M + H]+ |
| 65 | 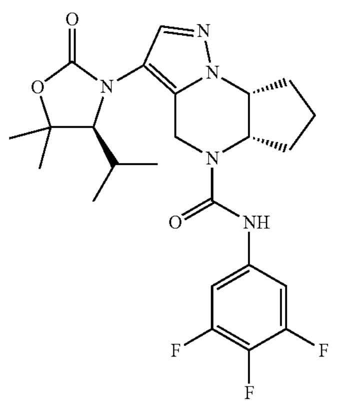 [SMILES: CC(C)[C@@H]1N(c2cnn3c2CN(C(=O)Nc2cc(F)c(F)c(F)c2)[C@H]2CCC[C@H]23)C(=O)OC1(C)C] | 492.35 [M + H]+ |
| 66 | 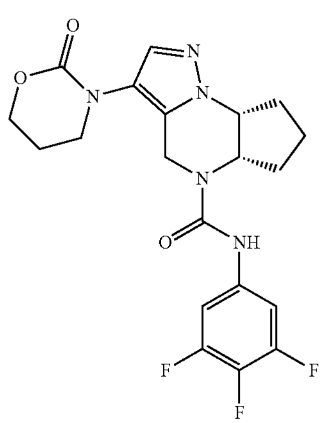 [SMILES: O=C1OCCCN1c1cnn2c1CN(C(=O)Nc1cc(F)c(F)c(F)c1)[C@H]1CCC[C@H]12] | 436.25 [M + H]+ |
| 67 | | 464.30 [M + H]+ |
| 68 | | 478.35 [M + H]+ |
| 69 | | 506.35 [M + H]+ |

-continued

| Example | Structure | ESIMS (M − H)⁻ or (M + H)⁺ |
|---|---|---|
| 70 | 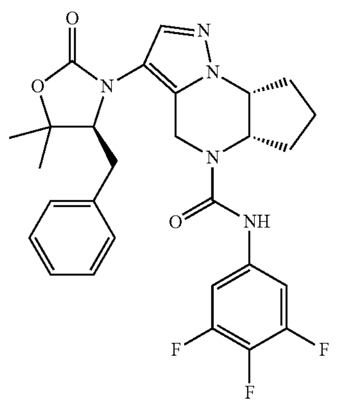 [SMILES: CC1(C)OC(=O)N(c2cnn3c2CN(C(=O)Nc2cc(F)c(F)c(F)c2)[C@H]2CCC[C@H]23)[C@H]1Cc1ccccc1] | 540.30 [M + H]⁺ |
| 71 | 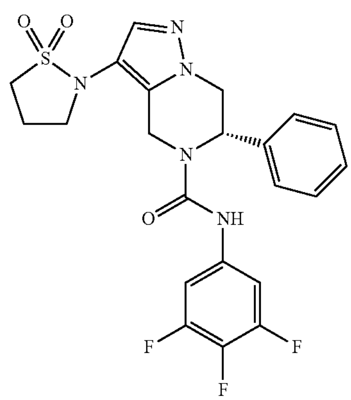 | 492.20 [M + H]⁺ |
| 72 | 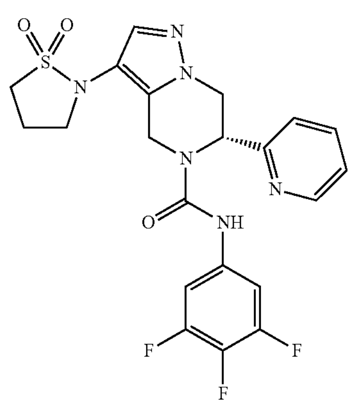 | 493.20 [M + H]⁺ |

-continued

| Example | Structure | ESIMS (M − H)⁻ or (M + H)⁺ |
|---|---|---|
| 73 | 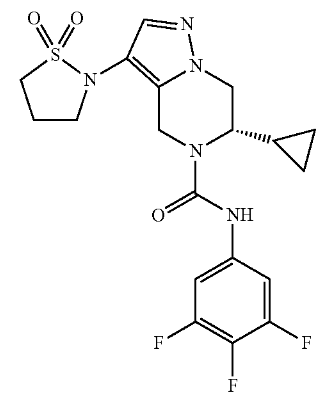 [SMILES: O=C(Nc1cc(F)c(F)c(F)c1)N1Cc2c(N3CCCS3(=O)=O)cnn2C[C@@H]1C1CC1] | 456.05 [M + H]⁺ |
| 74 | 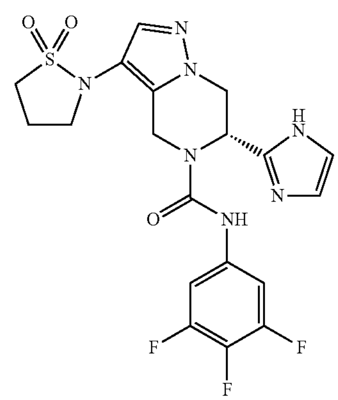 [SMILES: O=C(Nc1cc(F)c(F)c(F)c1)N1Cc2c(N3CCCS3(=O)=O)cnn2C[C@@H]1c1ncc[nH]1] | 482.10 [M + H]⁺ |
| 75 | 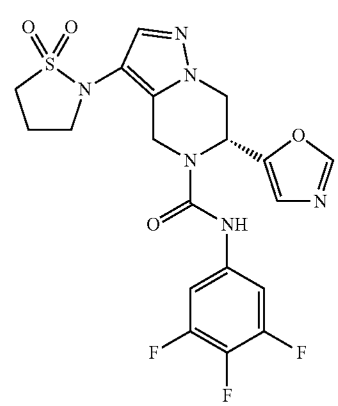 [SMILES: O=C(Nc1cc(F)c(F)c(F)c1)N1Cc2c(N3CCCS3(=O)=O)cnn2C[C@@H]1c1cnco1] | 483.20 [M + H]⁺ |

| Example | Structure | ESIMS (M − H)⁻ or (M + H)⁺ |
|---|---|---|
| 76 | 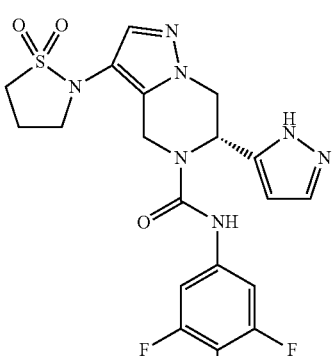 | [M + H]⁺ |
The following examples are prepared using procedures similar to those described above:
| Example | Structure |
|---|---|
| 20 | 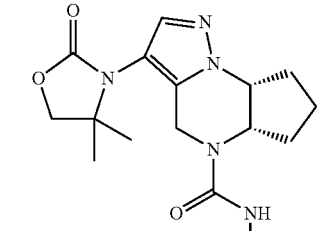 |
| 21 | 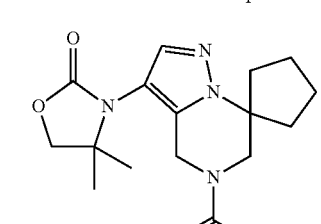 |
| 22 | 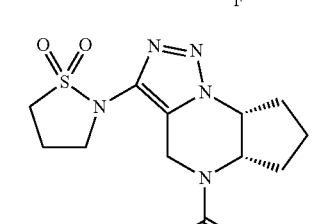 |
| 23 | 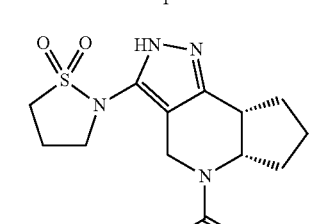 |
| 24 | 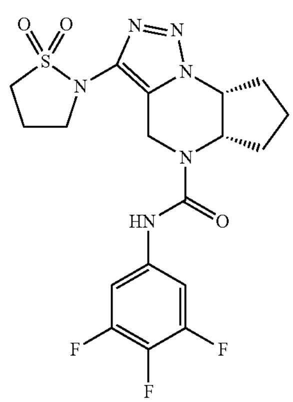 [SMILES: O=C(Nc1cc(F)c(F)c(F)c1)N1Cc2c(N3CCCS3(=O)=O)nnn2[C@@H]2CCC[C@@H]21] |
| 25 | 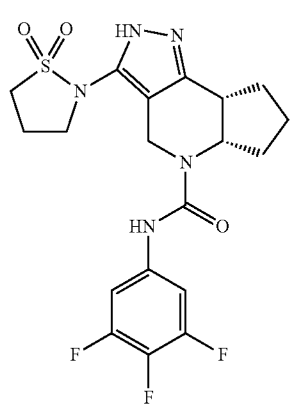 [SMILES: O=C(Nc1cc(F)c(F)c(F)c1)N1Cc2c(n[nH]c2N2CCCS2(=O)=O)[C@@H]2CCC[C@@H]21] |

-continued
| Example | Structure |
|---|---|
| 27 | 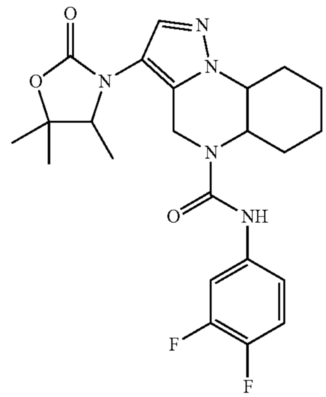 [SMILES: CC1N(c2cnn3c2CN(C(=O)Nc2ccc(F)c(F)c2)C2CCCCC23)C(=O)OC1(C)C] |
| 28 | 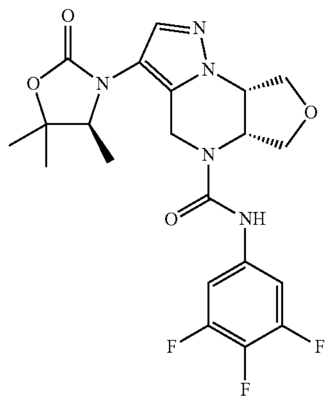 |
| 29 | 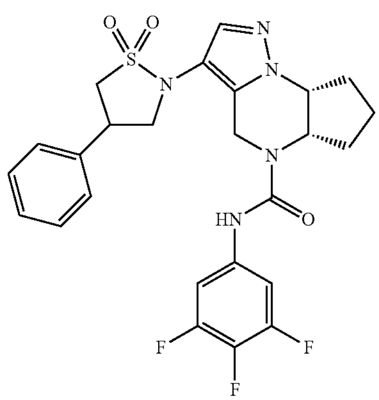 |
| 30 | 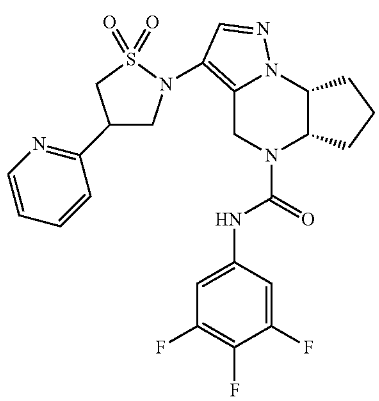 [SMILES: O=C(Nc1cc(F)c(F)c(F)c1)N1Cc2c(N3CC(c4ccccn4)CS3(=O)=O)cnn2[C@@H]2CCC[C@@H]21] |
-continued
| Example | Structure |
|---|---|
| 31 | 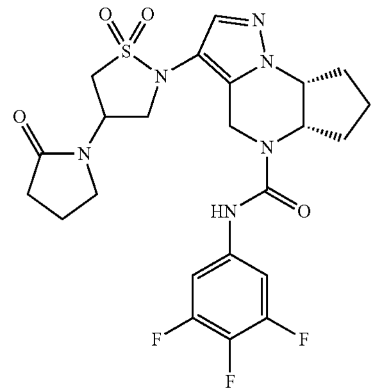 [SMILES: O=C1CCCN1C1CN(c2cnn3c2CN(C(=O)Nc2cc(F)c(F)c(F)c2)[C@H]2CCC[C@H]23)S(=O)(=O)C1] |
| 32 | 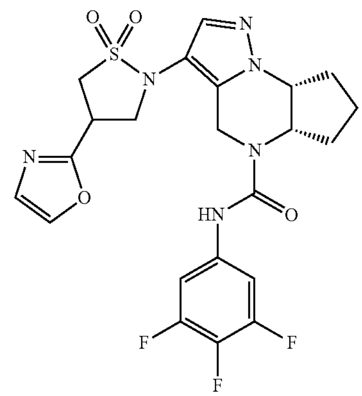 [SMILES: O=C(Nc1cc(F)c(F)c(F)c1)N1Cc2c(N3CC(c4ncco4)CS3(=O)=O)cnn2[C@@H]2CCC[C@@H]21] |
| 33 | 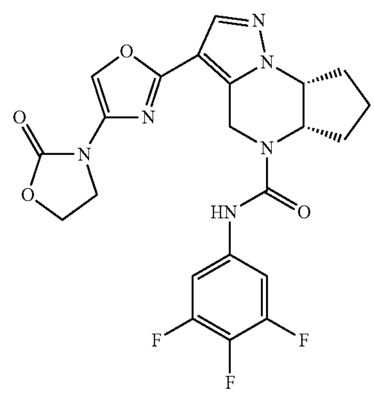 [SMILES: O=C1OCCN1c1coc(-c2cnn3c2CN(C(=O)Nc2cc(F)c(F)c(F)c2)[C@H]2CCC[C@H]23)n1] |
| 34 | 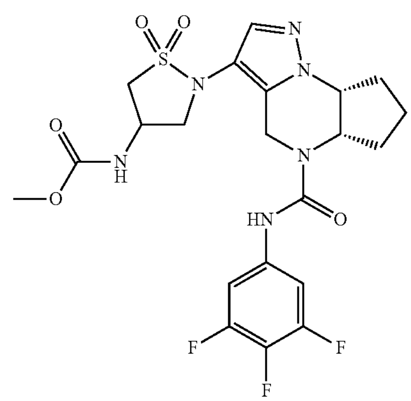 [SMILES: COC(=O)NC1CN(c2cnn3c2CN(C(=O)Nc2cc(F)c(F)c(F)c2)[C@H]2CCC[C@H]23)S(=O)(=O)C1] |
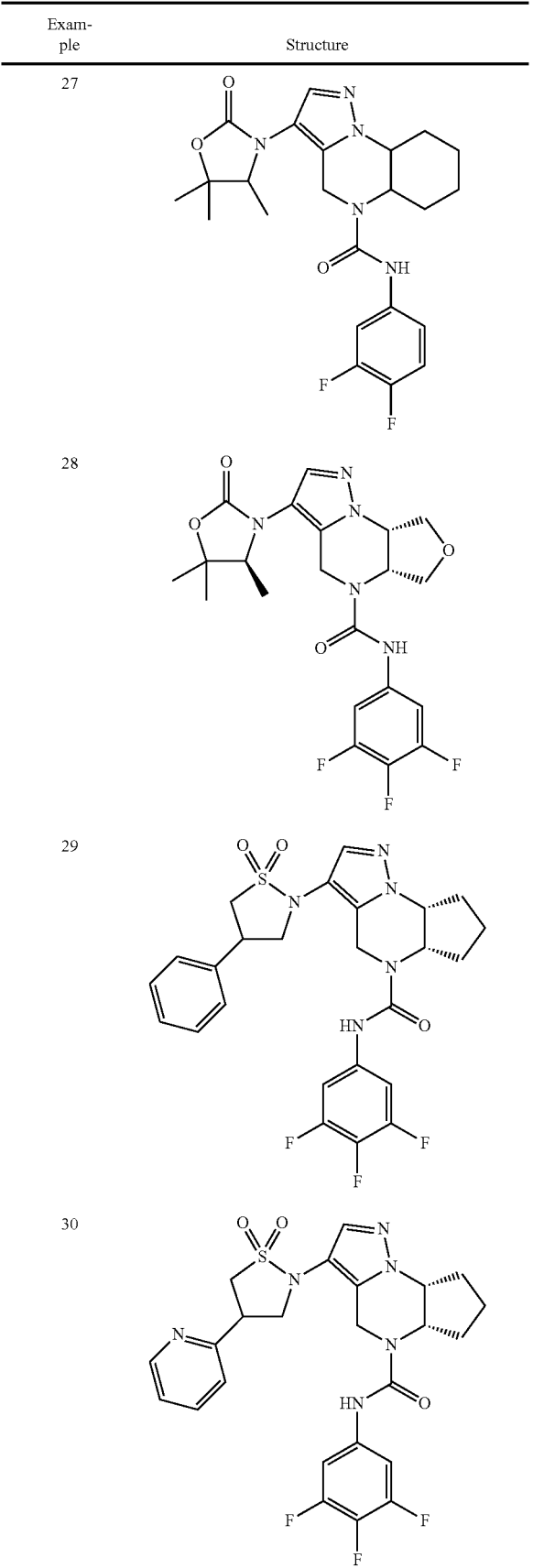
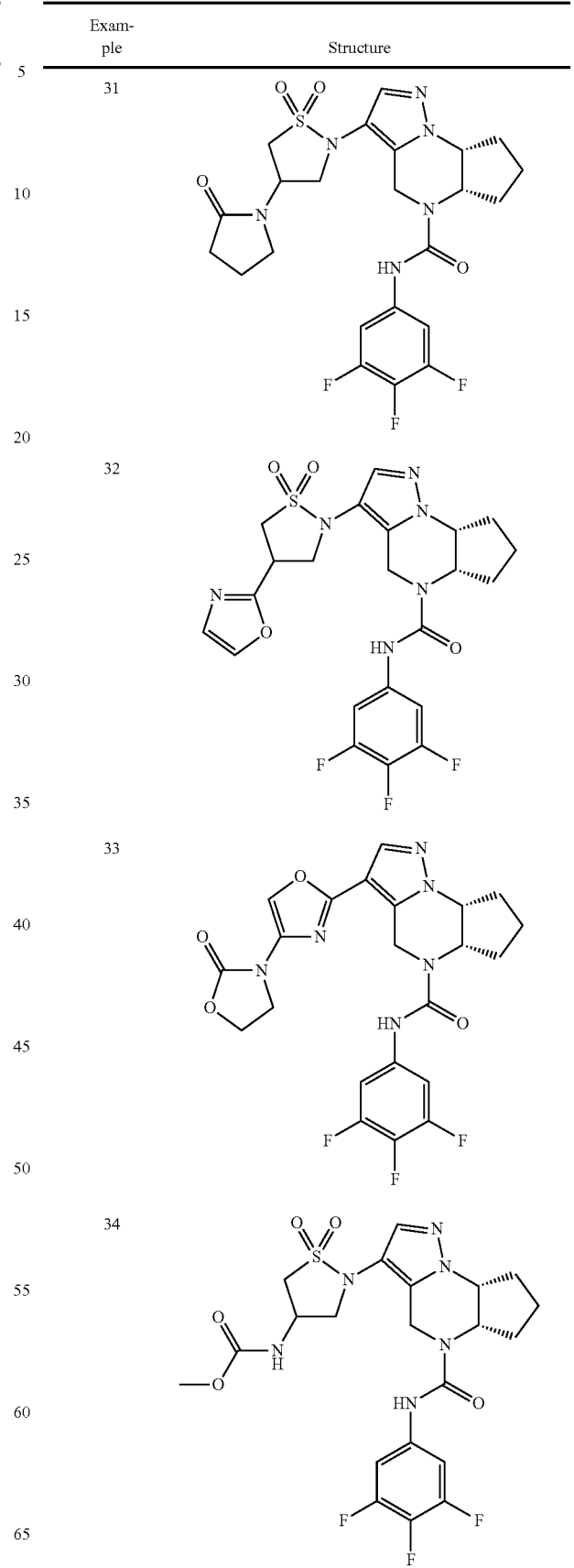

| Example | Structure |
|---|---|
| 35 | (structure with methyl carbamate pyrrolidine, pyrazolo-pyrazine bicyclic core, and 3,4,5-trifluorophenyl urea) |

BIOLOGICAL ACTIVITY

Methods: HepAD38 cells were maintained as previously reported (Ladner et al, *Antimicrob. Agents Chemother.* 1997, 4, 1715). Briefly, cells were passaged upon attaining confluency in DMEM/F12 media in the presence of 10% FBS, Penn/Strep, 250 µg/mL G418, and 1 ug/ml tetracycline. Compounds were screened by first washing cells three times with PBS to remove tetracycline, and plating in 96 well plates at 35,000 cells/well. Compounds dissolved in DMSO were then diluted 1:200 into wells containing cells. Five days after compound addition, material was harvested for analysis. For an extended 8 day analysis, cells were plated and treated as described above, but media and compound were refreshed on day 2 and day 5 post initial treatment.

On harvest day, virion DNA was obtained by lysing with Sidestep Lysis and Stabilization Buffer and then quantified via quantitative real time PCR. Commercially available ELISA kits were used to quantitate the viral proteins HBsAg (Alpco) or HbeAg (US Biological) by following the manufacturer's recommended protocol after diluting samples to match the linear range of their respective assays. Irrespective of readout, compound concentrations that reduce viral product accumulation in the cell lysates or supernatants by 50% relative to no drug controls ($EC_{50}$) are reported; $EC_{50}$ ranges are as follows: A<0.1 µM; B 0.1-0.2 µM; C>0.2 µM.

Compound toxicity was evaluated by seeding cells at 15,000 cells/well and treating with compound as described above. Three days after compound addition, cells were treated with ATPLite reagent and compound concentrations that reduce total ATP levels in wells by 50% relative to no drug controls ($CC_{50}$) are reported; $CC_{50}$ ranges are as follows: A>25 µM; B 10-25 µM; C<10 µM.

TABLE 1

Summary of Activities

| Compd. Number | HepAD38 $EC_{50}$ (µM) | Compd. Number | HepAD38 $EC_{50}$ (µM) |
|---|---|---|---|
| 1 | C | 2 | C |
| 3 | C | 4 | A |
| 5 | B | 6 | A |
| 7 | B | 8 | A |
| 9 | C | 10 | A |
| 11 | A | 12 | A |
| 13 | A | 14 | A |
| 15 | A | 16 | C |
| 17 | A | 18 | A |
| 19 | A | 26 | A |
| 36 | C | 37 | A |
| 38 | B | 39 | A |
| 40 | A | 41 | C |
| 42 | B | 43 | C |
| 44 | A | 45 | A |
| 46 | C | 47 | C |
| 48 | A | 49 | B |
| 50 | A | 51 | A |
| 52 | C | 53 | A |
| 54 | A | 55 | A |
| 56 | B | 57 | A |
| 58 | B | 59 | A |
| 60 | A | 61 | B |
| 62 | C | 63 | C |
| 64 | B | 65 | A |
| 66 | B | 67 | A |
| 68 | B | 69 | C |
| 70 | A | 71 | A |
| 72 | A | 73 | A |
| 74 | C | 75 | B |
| 76 | C | | |

TABLE 2

Summary of Cytotoxicity

| Compd. Number | ATPlite $CC_{50}$ (µM) | Compd. Number | ATPlite $CC_{50}$ (µM) |
|---|---|---|---|
| 10 | A | 11 | A |
| 12 | A | 15 | A |
| 17 | A | 18 | A |
| 19 | A | 26 | A |
| 51 | A | 53 | A |
| 60 | A | 72 | A |
| 73 | A | | |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I), or a pharmaceutically acceptable salt thereof:

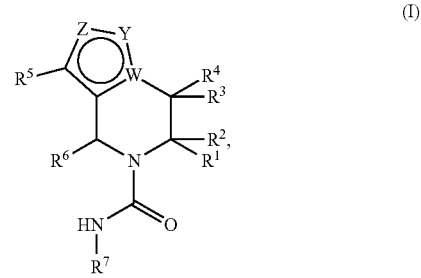

wherein:
W and Y are N and Z is $CR^{10}$; or
W is C, one of Y and Z is N and the other is $NR^{11}$; or W, Y and Z are each N;

R¹⁰ is hydrogen, halo, or optionally substituted $C_1$-$C_6$ alkyl;

R¹¹ is hydrogen, optionally substituted $C_1$-$C_6$ alkyl, or optionally substituted $C_3$-$C_8$ cycloalkyl; or R¹ and R³ are independently hydrogen or optionally substituted $C_1$-$C_6$ alkyl;

R² is selected from the group consisting of optionally substituted $C_3$-$C_6$ cycloalkyl, optionally substituted 3- to 8-membered heterocyclic, optionally substituted aryl, and optionally substituted heteroaryl;

R⁴ is selected from the group consisting of hydrogen, halo, hydroxy, protected hydroxy, amino, optionally substituted amino, optionally substituted $C_1$-$C_6$ alkyl, and optionally substituted $C_1$-$C_6$ alkoxy;

Alternatively, R¹ and R² are taken together with the carbon atom to which they are attached to form optionally substituted $C_3$-$C_8$ cycloalkyl, optionally substituted $C_3$-$C_8$ cycloalkenyl, or optionally substituted 3- to 8-membered heterocyclic;

Alternatively, R¹ and R³ are taken together with the carbon atoms to which they are attached to form an olefinic double bond;

Alternatively, R² and R⁴ are taken together with the carbon atoms to which they are attached to form optionally substituted $C_3$-$C_8$ cycloalkyl, optionally substituted $C_3$-$C_8$ cycloalkenyl, or optionally substituted 3- to 8-membered heterocyclic;

Alternatively, R³ and R⁴ are taken together with the carbon atom to which they are attached to form optionally substituted $C_3$-$C_8$ cycloalkyl, optionally substituted $C_3$-$C_8$ cycloalkenyl, or optionally substituted 3- to 8-membered heterocyclic;

Alternatively, R¹, R², R³ and R⁴ are taken together with the carbon atoms to which they are attached to form optionally substituted aryl or optionally substituted heteroaryl;

R⁵ is selected from the group consisting of optionally substituted $C_1$-$C_6$ alkyl, optionally substituted $C_2$-$C_8$ alkenyl, optionally substituted $C_2$-$C_8$ alkynyl, optionally substituted $C_3$-$C_8$ cycloalkyl, optionally substituted 3- to 8-membered heterocyclic, optionally substituted aryl, optionally substituted heteroaryl, and -L-R¹²; wherein L is selected from a group consisting of —O—, —S—, —NR¹¹—, —C(O)—, —C(O)O—, —OC(O)—, —C(O)N(R¹¹)—, —N(R¹¹)C(O)—, —OC(O)N(R¹¹)—, —N(R¹¹)C(O)O—, —N(R¹¹)C(O)N(R¹¹)—, —S(O)—, —S(O)₂—, —S(O)₂N(R¹¹)—, —N(R¹¹)S(O)₂—, optionally substituted $C_1$-$C_6$ alkyl, optionally substituted $C_2$-$C_8$ alkenyl, optionally substituted $C_2$-$C_8$ alkynyl, optionally substituted $C_3$-$C_8$ cycloalkyl, optionally substituted 3- to 8-membered heterocyclic, optionally substituted aryl, and optionally substituted heteroaryl;

R¹² is selected from the group consisting of hydrogen, optionally substituted $C_1$-$C_6$ alkyl, optionally substituted $C_3$-$C_8$ cycloalkyl, optionally substituted 3- to 8-membered heterocyclic, optionally substituted aryl, and optionally substituted heteroaryl;

R⁶ is hydrogen or optionally substituted $C_1$-$C_6$ alkyl; and

R⁷ is an optionally substituted aryl, optionally substituted heteroaryl, optionally substituted $C_1$-$C_6$ alkyl, or optionally substituted $C_3$-$C_8$ cycloalkyl.

2. The compound of claim 1, wherein R⁵ is selected from one of the following by removal of one hydrogen atom:

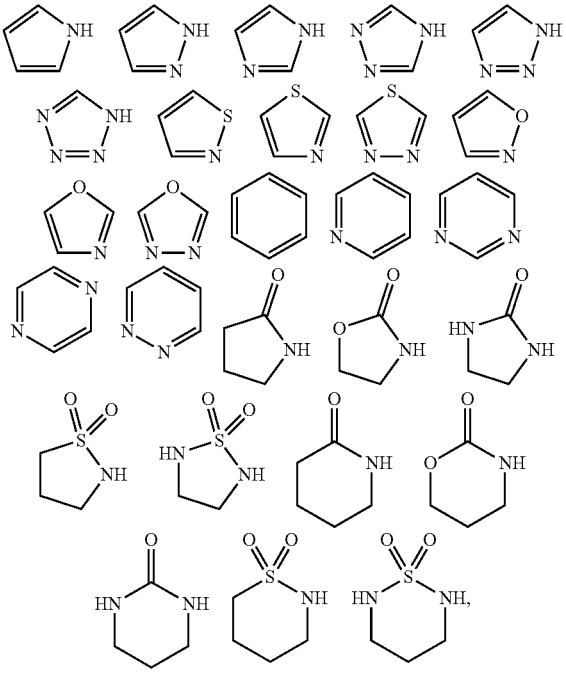

each of the above shown groups is optionally substituted and is connected to the pyrazole or triazole ring through a carbon atom or, if possible, a nitrogen atom.

3. The compound of claim 1, wherein R⁵ is -L-R¹², wherein -L- is —O—, —N(R¹)C(O)—, —OC(O)N(R¹)—, —N(R¹¹)C(O)O—, —N(R¹¹)C(O)N(R¹¹)—, —N(R¹¹)S(O)₂—, or one of the following by removal of two hydrogen atoms:

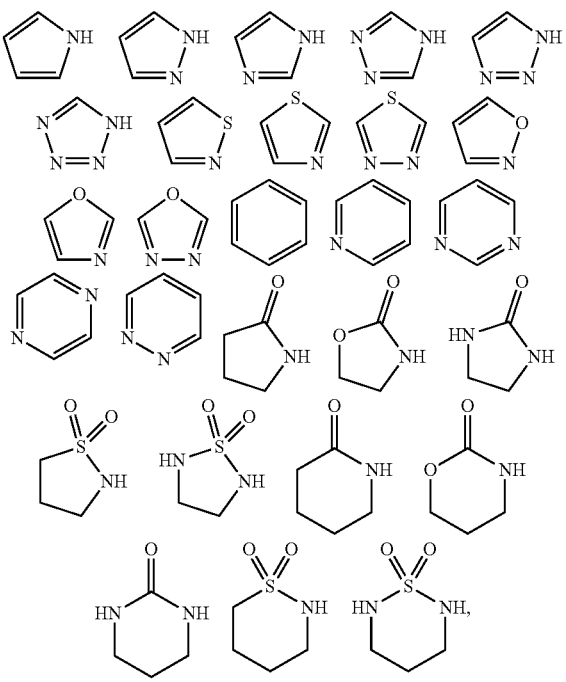

wherein each of the above shown groups is optionally substituted; and $R^{12}$ is selected from one of the following by removal of one hydrogen atom:
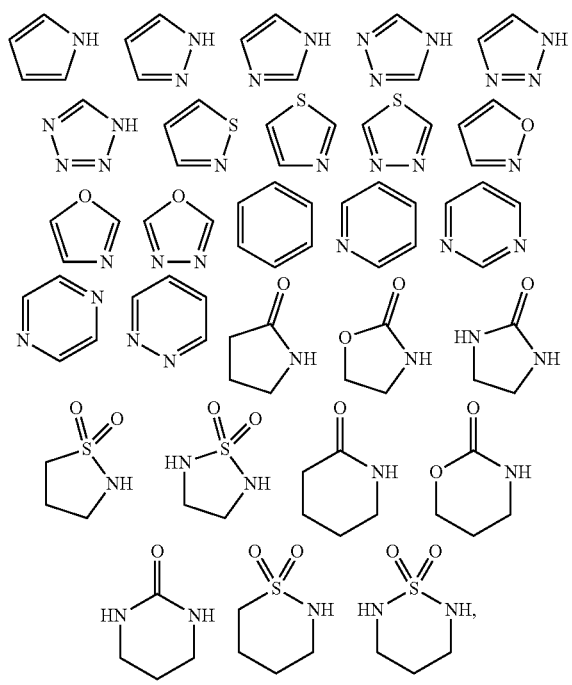
wherein each of the above shown groups is optionally substituted.
4. The compound of claim 1, wherein $R^7$ is selected from the group consisting of:
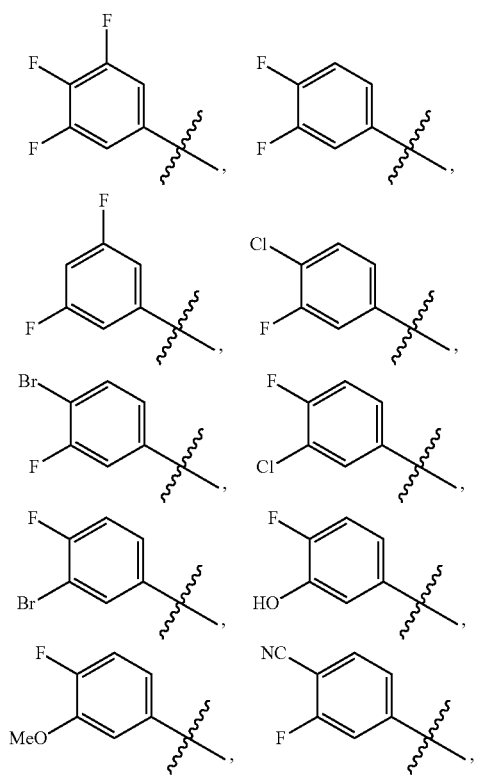
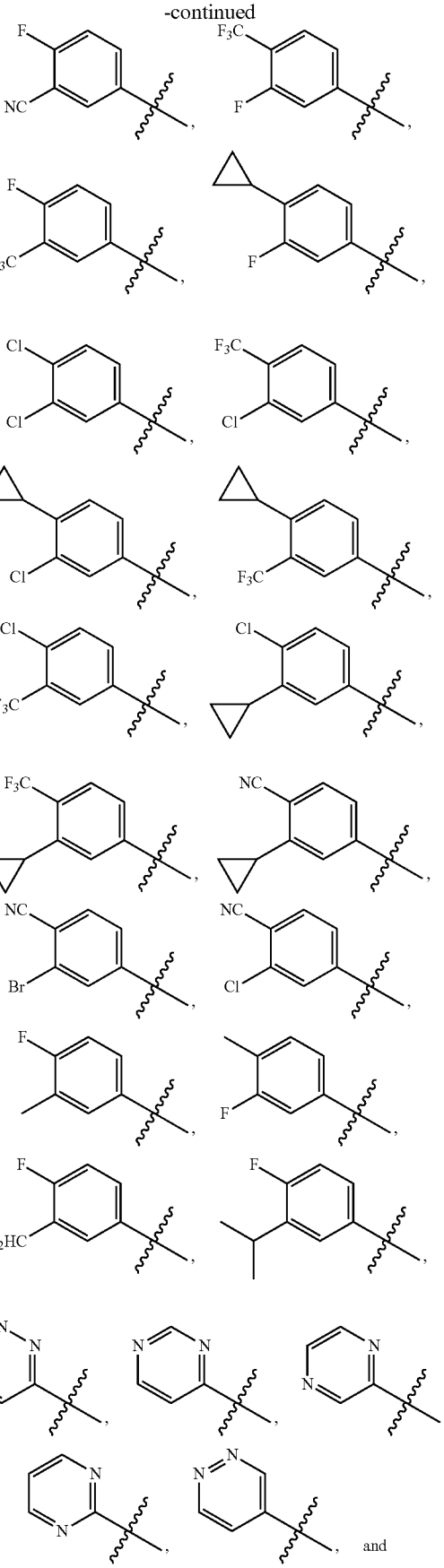

-continued

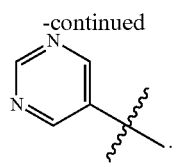

5. The compound of claim 1, represented by Formula (IIa), or a pharmaceutically acceptable salt thereof, (IIa)

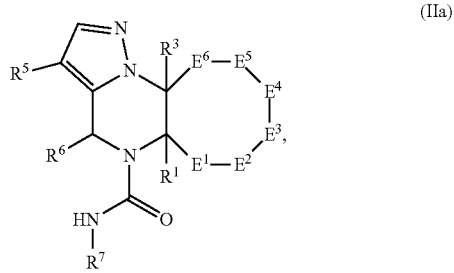

wherein $E^1$, $E^2$, $E^3$, $E^4$, $E^5$, and $E^6$ are each independently selected from the group consisting of absent, —$CR^{13}R^{14}$—, —$NR^{11}$—, —O—, —C(O)—, —S(O)—, S(O)—, —$S(O)_2$—, and —S—, provided that at least one of $E^1$, $E^2$, $E^3$, $E^4$, $E^5$, and $E^6$ is not absent; $R^{13}$ and $R^{14}$ at each occurrence are independently hydrogen, halo, or optionally substituted $C_1$-$C_6$ alkyl; and $R^1$, $R^3$, $R^5$, $R^6$, and $R^7$ are as defined claim 1.

6. The compound of claim 1, represented by Formula (IIIa) or Formula (IVa), or a pharmaceutically acceptable salt thereof, (IIIa)

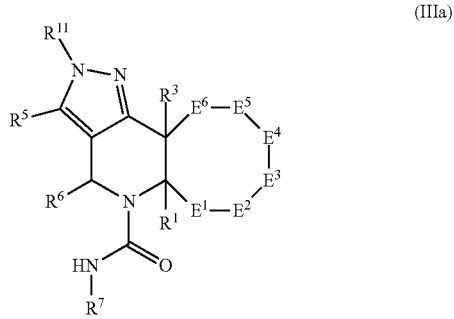

(IVa)

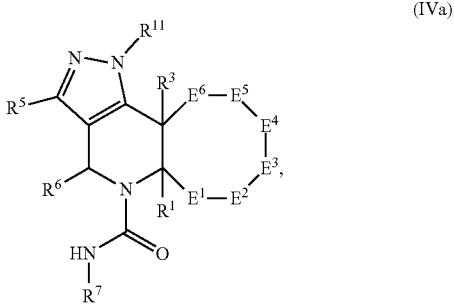

wherein $E^1$, $E^2$, $E^3$, $E^4$, $E^5$, and $E^6$ are each independently selected from the group consisting of absent, —$CR^{13}R^{14}$—, —$NR^{11}$—, —O—, —C(O)—, S(O)—, —$S(O)_2$—, and —S—, provided that at least one of $E^1$, $E^2$, $E^3$, $E^4$, $E^5$, and $E^6$ is not absent; $R^{13}$ and $R^{14}$ at each occurrence are independently hydrogen, halo, or optionally substituted $C_1$-$C_6$ alkyl; and $R^1$, $R^3$, $R^{11}$, $R^5$, $R^6$, and $R^7$ are as defined claim 1.

7. The compound of claim 1, represented by Formula (Va), or a pharmaceutically acceptable salt thereof, (Va)

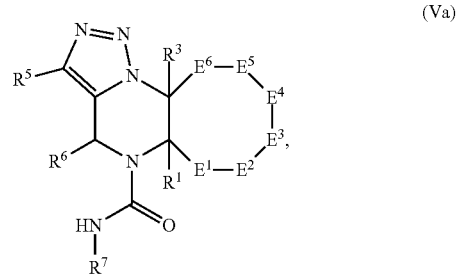

wherein $E^1$, $E^2$, $E^3$, $E^4$, $E^5$, and $E^6$ are each independently selected from the group consisting of absent, —$CR^{13}R^{14}$—, —$NR^{11}$—, —O—, —C(O)—, —S(O)—, S(O)—, —$S(O)_2$—, and —S—, provided that at least one of $E^1$, $E^2$, $E^3$, $E^4$, $E^5$, and $E^6$ is not absent; $R^{13}$ and $R^{14}$ at each occurrence are independently hydrogen, halo, or optionally substituted $C_1$-$C_6$ alkyl; and $R^1$, $R^3$, $R^5$, $R^6$, and $R^7$ are as defined claim 1.

8. The compound of claim 1, represented by Formula (VI), or a pharmaceutically acceptable salt thereof, (VI)

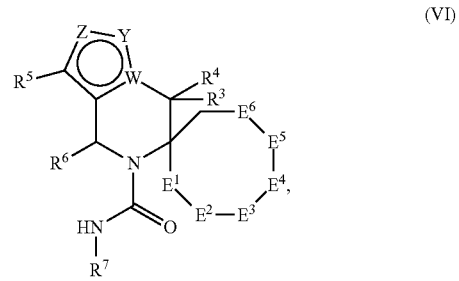

wherein at least one of $E^1$, $E^2$, $E^3$, $E^5$, and $E^6$ is present, and $E^1$, $E^2$, $E^3$, $E^5$, and $E^6$ are each independently selected from the group consisting of absent, —$CR^{13}R^{14}$—, —$NR^{11}$—, —O—, —C(O)—, —S(O)—, —$S(O)_2$—, and —S—, provided that at least one of $E^1$, $E^2$, $E^3$, $E^4$, $E^5$, and $E^6$ is not absent; $R^{13}$ and $R^{14}$ at each occurrence are independently hydrogen, halo, or optionally substituted $C_1$-$C_6$ alkyl; W, Y, Z, $R^3$, $R^4$, $R^5$, $R^6$, and $R^7$ are as defined claim 1.

9. The compound of claim 1, represented by Formula (VIIa), Formula (VIIb), Formula (VIIc), or Formula (VIId), or a pharmaceutically acceptable salt thereof, (VIIa)

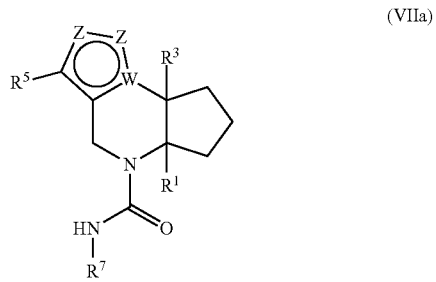

-continued
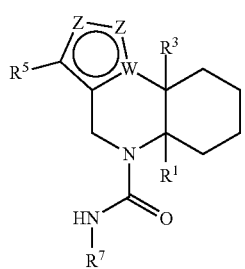
(VIIb)
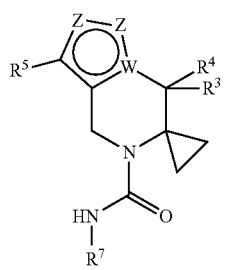
(VIIc)
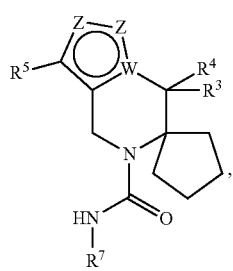
(VIId)
wherein W, Y, Z, $R^1$, $R^3$, $R^4$, $R^5$, and $R^7$ are as defined claim 1.
10. The compound of claim 1, selected from the compounds set forth below or a pharmaceutically acceptable salt thereof:
| Compound | Structure |
|---|---|
| 1 | 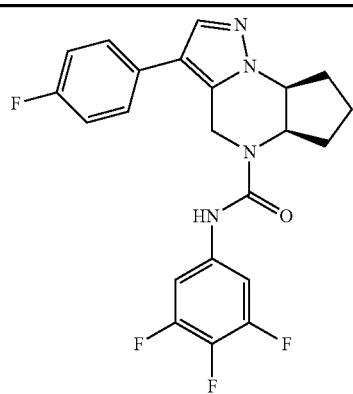 |
-continued
| Compound | Structure |
|---|---|
| 2 | 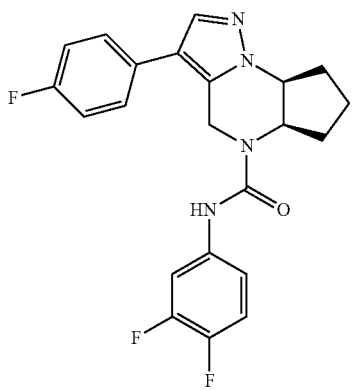 [SMILES: O=C(Nc1ccc(F)c(F)c1)N1Cc2c(-c3ccc(F)cc3)cnn2[C@H]2CCC[C@H]21] |
| 3 | 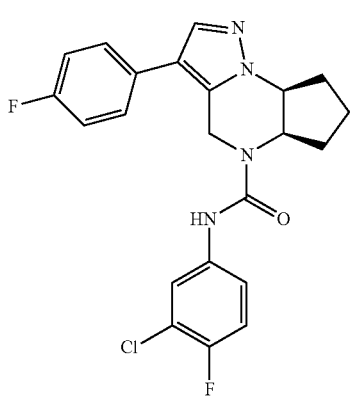 [SMILES: O=C(Nc1ccc(F)c(Cl)c1)N1Cc2c(-c3ccc(F)cc3)cnn2[C@H]2CCC[C@H]21] |
| 4 | 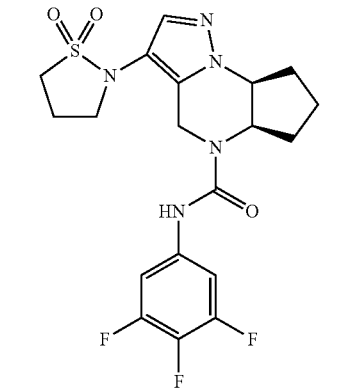 [SMILES: O=C(Nc1cc(F)c(F)c(F)c1)N1Cc2c(N3CCCS3(=O)=O)cnn2[C@H]2CCC[C@H]21] |
| 5 | 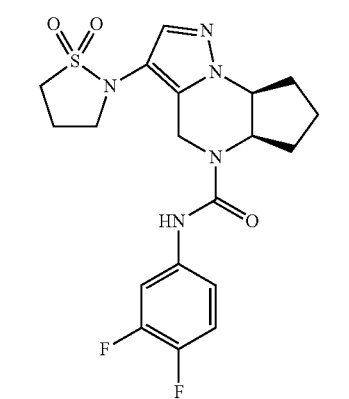 |

-continued
| Compound | Structure |
|---|---|
| 6 | 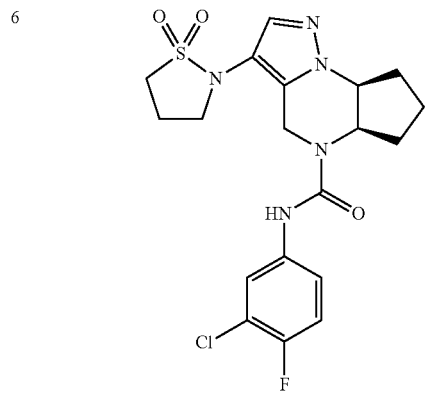 |
| 7 | 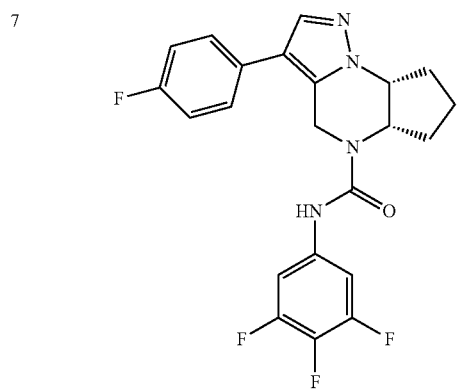 |
| 8 | 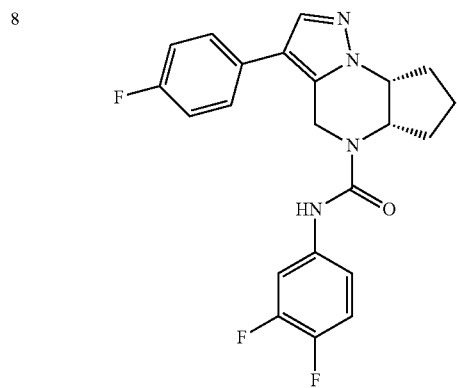 |
| 9 | 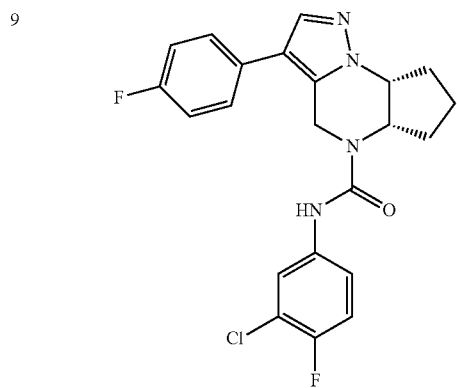 |
-continued
| Compound | Structure |
|---|---|
| 10 | 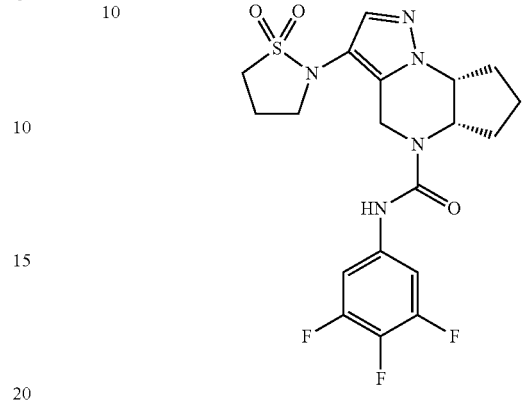 |
| 11 | 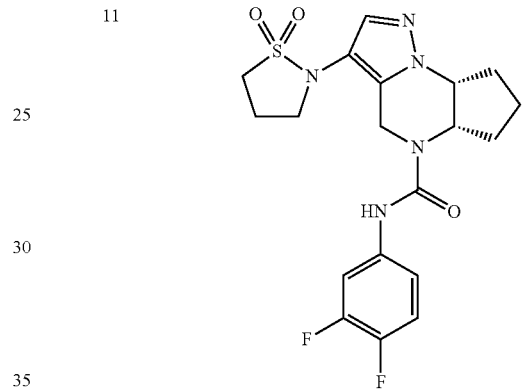 |
| 12 | 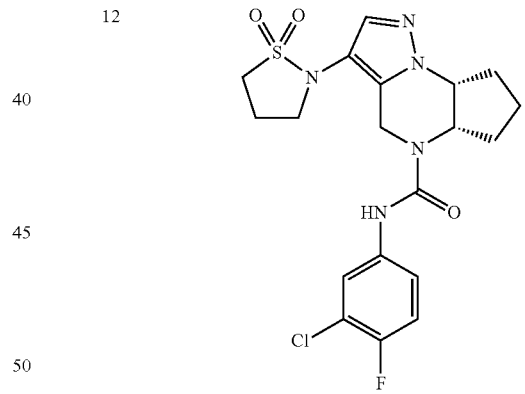 |
| 13 | 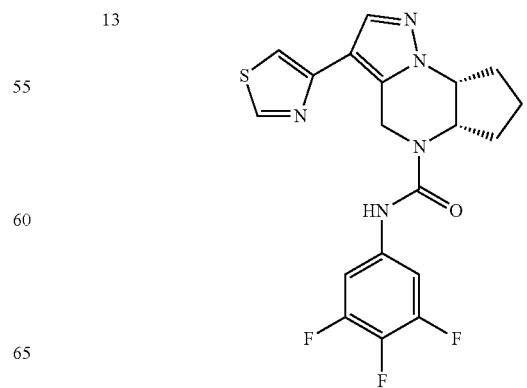 |

| Compound | Structure |
|---|---|
| 14 | 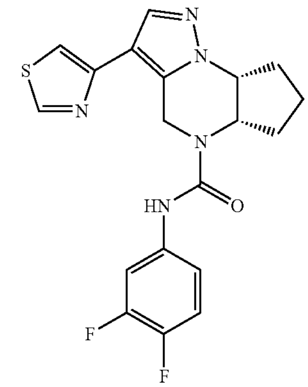 [SMILES: O=C(Nc1ccc(F)c(F)c1)N1Cc2c(-c3cscn3)cnn2[C@@H]2CCC[C@@H]21] |
| 15 | 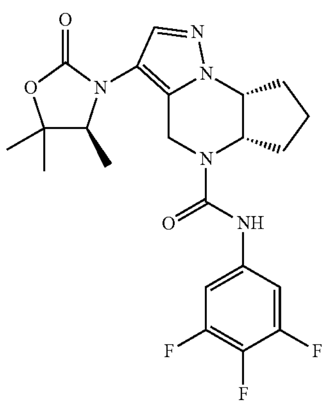 [SMILES: C[C@@H]1N(c2cnn3c2CN(C(=O)Nc2cc(F)c(F)c(F)c2)[C@H]2CCC[C@H]23)C(=O)OC1(C)C] |
| 16 | 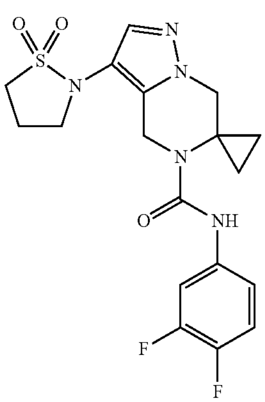 [SMILES: O=C(Nc1ccc(F)c(F)c1)N1Cc2c(N3CCCS3(=O)=O)cnn2CC12CC2] |
| 17 | 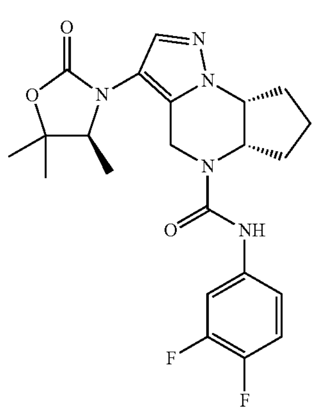 [SMILES: C[C@@H]1N(c2cnn3c2CN(C(=O)Nc2ccc(F)c(F)c2)[C@H]2CCC[C@H]23)C(=O)OC1(C)C] |
| 18 | |
| 21 | |
| 22 | |
| 23 | |

| Compound | Structure |
|---|---|
| 24 | 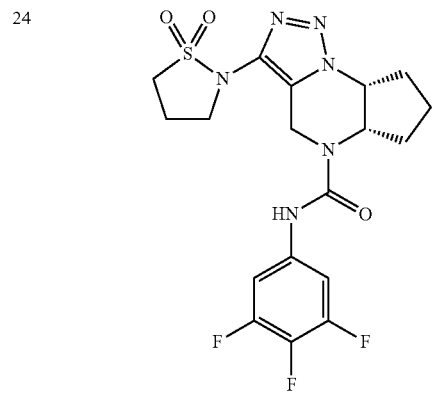 |
| 25 | 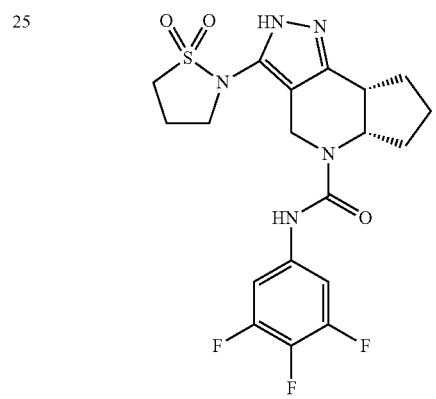 |
| 26 | 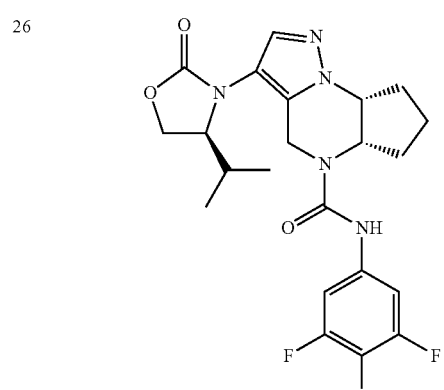 |
| 27 | 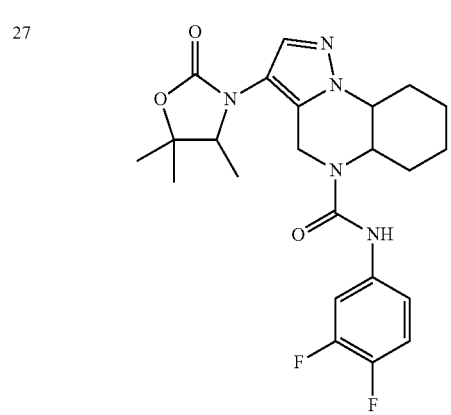 |
| 28 | 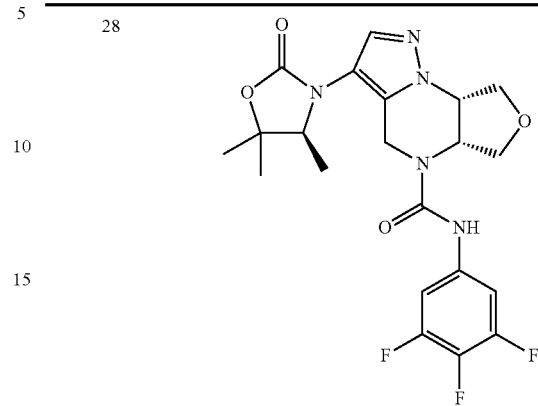 |
| 29 | 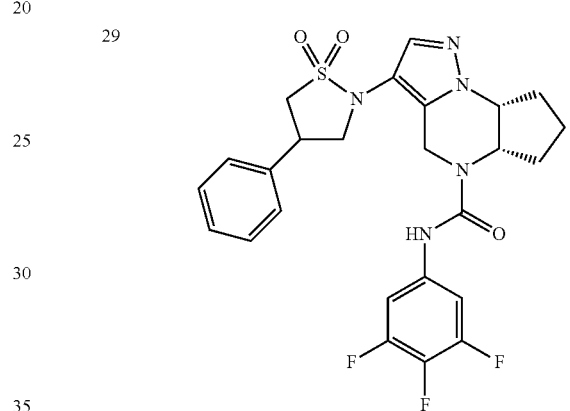 |
| 30 | 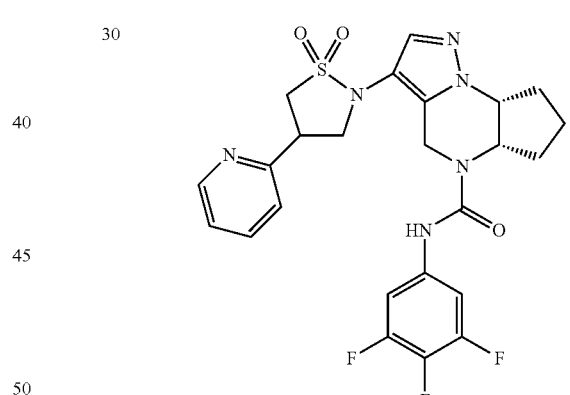 |
| 31 | 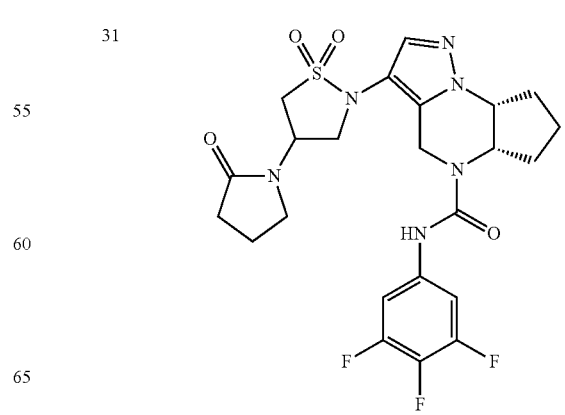 |

85
-continued
| Compound | Structure |
|---|---|
| 32 | 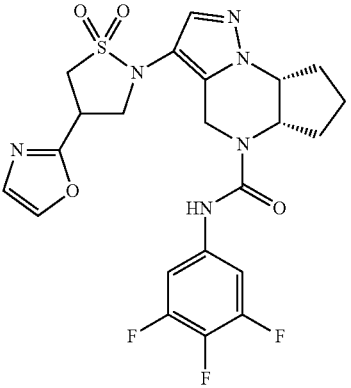 [SMILES: O=C(Nc1cc(F)c(F)c(F)c1)N1Cc2c(N3CC(c4ncco4)CS3(=O)=O)cnn2[C@@H]2CCC[C@@H]21] |
| 33 | 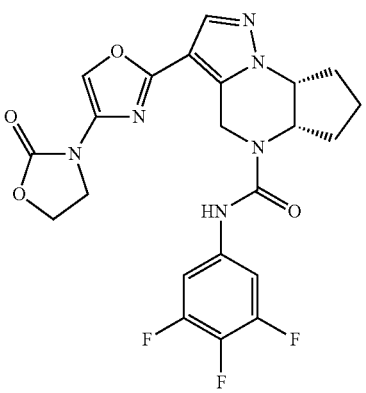 |
| 34 | 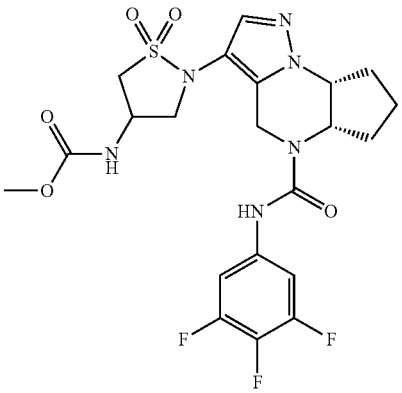 [SMILES: COC(=O)NC1CN(c2cnn3c2CN(C(=O)Nc2cc(F)c(F)c(F)c2)[C@H]2CCC[C@H]23)S(=O)(=O)C1] |
| 35 | 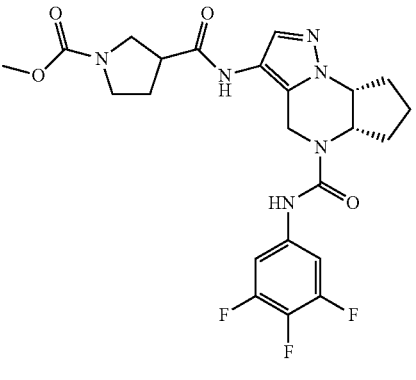 [SMILES: COC(=O)N1CCC(C(=O)Nc2cnn3c2CN(C(=O)Nc2cc(F)c(F)c(F)c2)[C@H]2CCC[C@H]23)C1] |
86
-continued
| Compound | Structure |
|---|---|
| 36 | 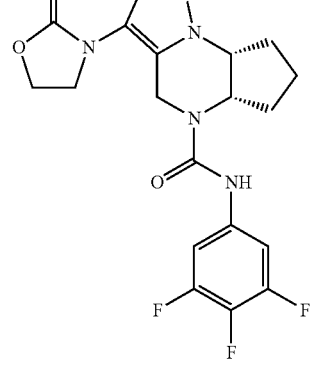 |
| 37 | 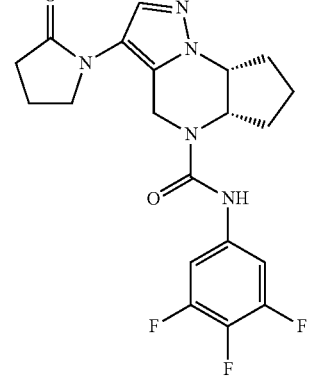 |
| 38 | 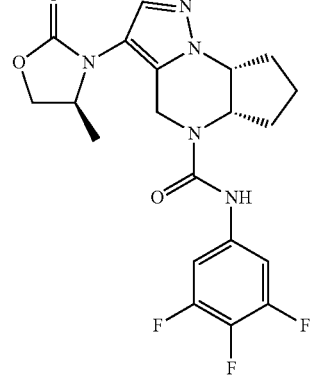 |
| 39 | 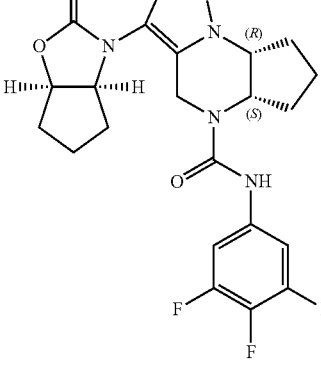 |

| Compound | Structure |
|---|---|
| 40 | 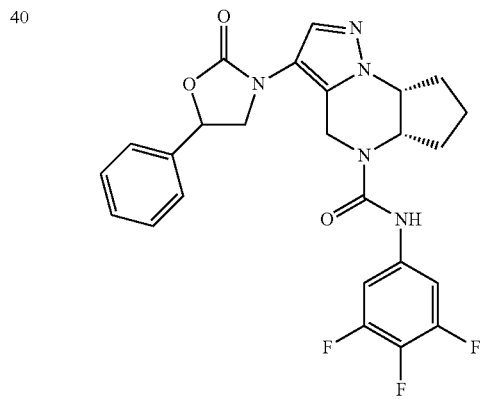 |
| 41 | 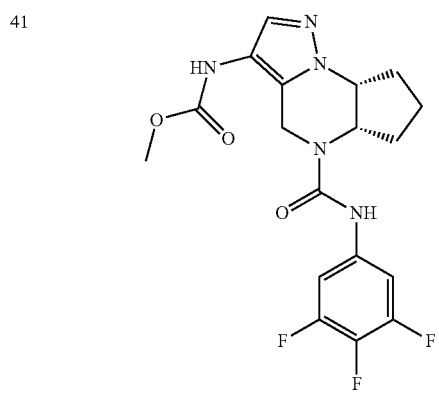 |
| 42 | 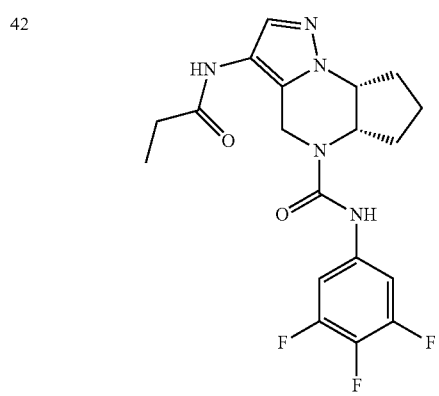 |
| 43 | 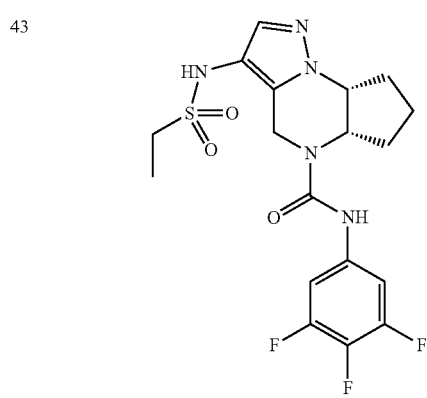 |
| Compound | Structure |
|---|---|
| 44 | 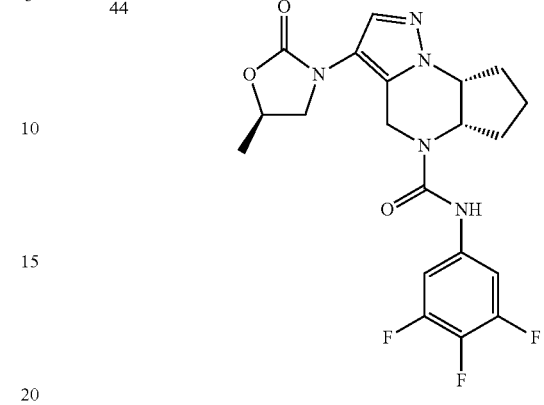 |
| 45 | 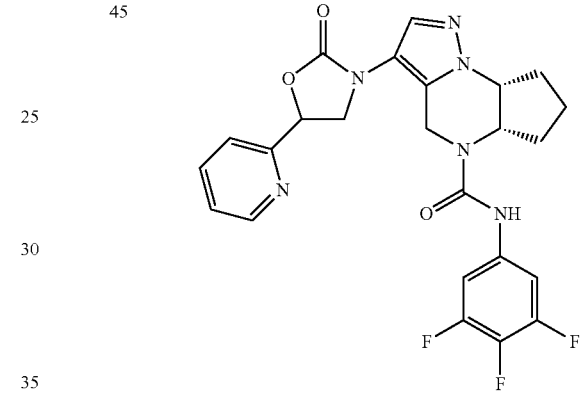 |
| 46 | 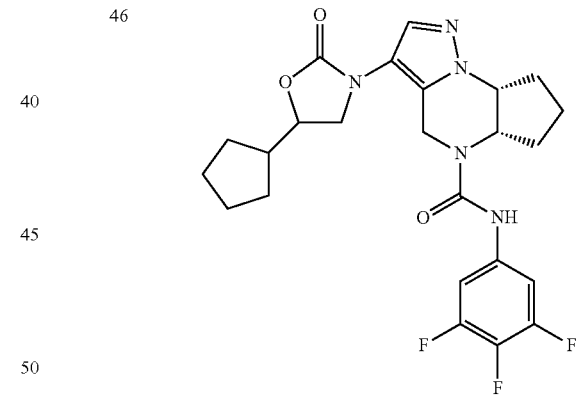 |
| 47 | 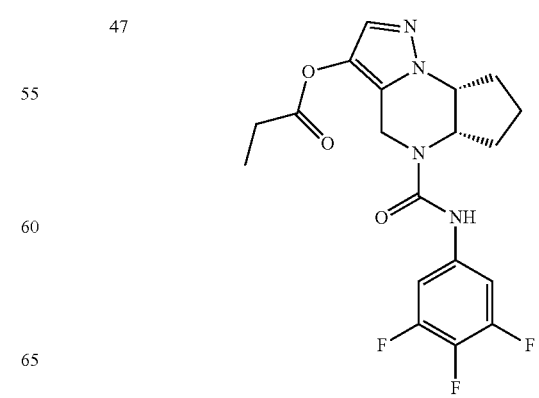 |

| Compound | Structure |
|---|---|
| 48 | (structure) |
| 49 | (structure) |
| 50 | (structure) |
| 51 | (structure) |
| 52 | (structure) |
| 53 | (structure) |
| 54 | (structure) |
| 55 | (structure) |

-continued

| Compound | Structure |
|---|---|
| 56 | 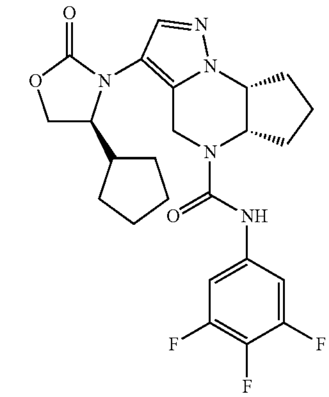 [SMILES: O=C(Nc1cc(F)c(F)c(F)c1)N1Cc2c(N3C(=O)OC[C@@H]3C3CCCC3)cnn2[C@@H]2CCC[C@@H]21] |
| 57 | 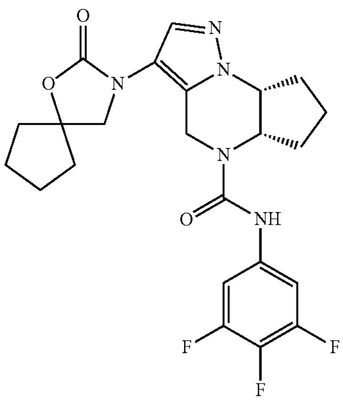 [SMILES: O=C1OC2(CCCC2)CN1c1cnn2c1CN(C(=O)Nc1cc(F)c(F)c(F)c1)[C@H]1CCC[C@H]12] |
| 58 | 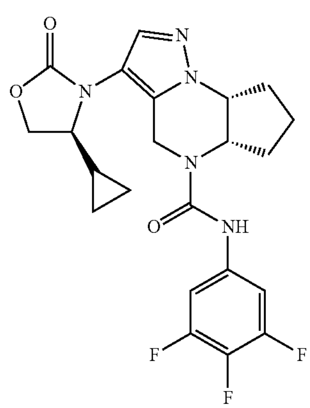 [SMILES: O=C(Nc1cc(F)c(F)c(F)c1)N1Cc2c(N3C(=O)OC[C@@H]3C3CC3)cnn2[C@@H]2CCC[C@@H]21] |
| 59 | 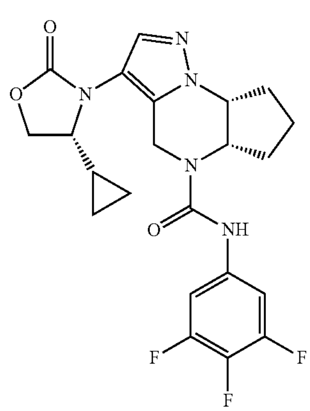 [SMILES: O=C(Nc1cc(F)c(F)c(F)c1)N1Cc2c(N3C(=O)OC[C@H]3C3CC3)cnn2[C@@H]2CCC[C@@H]21] |
| 60 | |
| 61 | |
| 62 | |
| 63 | |

| Compound | Structure |
|---|---|
| 64 | 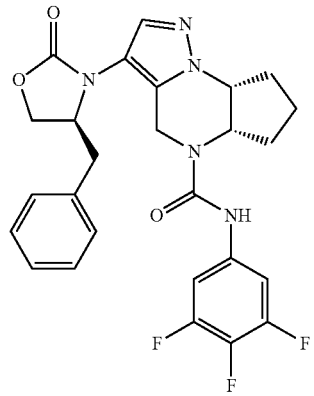 [SMILES: O=C(Nc1cc(F)c(F)c(F)c1)N1Cc2c(N3C(=O)OC[C@@H]3Cc3ccccc3)cnn2[C@@H]2CCC[C@@H]21] |
| 65 | 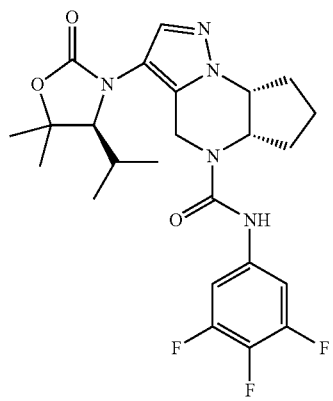 [SMILES: CC(C)[C@@H]1N(c2cnn3c2CN(C(=O)Nc2cc(F)c(F)c(F)c2)[C@H]2CCC[C@H]23)C(=O)OC1(C)C] |
| 66 | 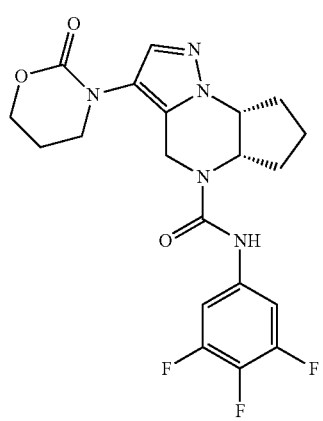 [SMILES: O=C1OCCCN1c1cnn2c1CN(C(=O)Nc1cc(F)c(F)c(F)c1)[C@H]1CCC[C@H]12] |
| Compound | Structure |
|---|---|
| 67 | 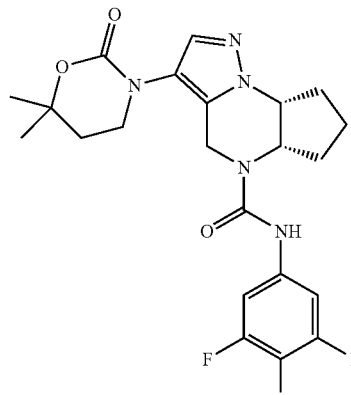 |
| 68 | 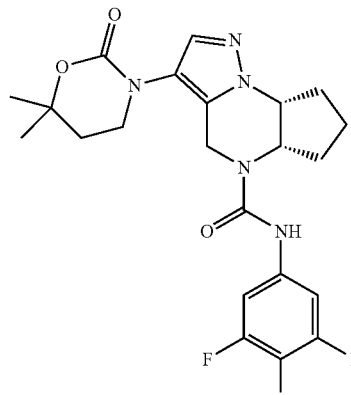 |
| 69 | 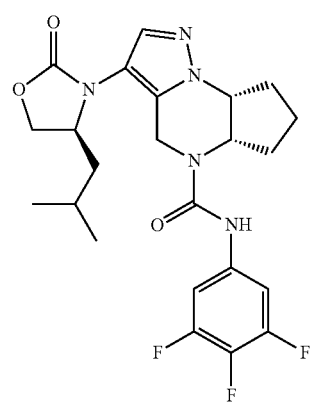 [SMILES: CC(C)C[C@H]1COC(=O)N1c1cnn2c1CN(C(=O)Nc1cc(F)c(F)c(F)c1)[C@H]1CCC[C@H]12] |

| Compound | Structure |
|---|---|
| 70 | (structure) |
| 71 | (structure) |
| 72 | (structure) |
| 73 | (structure) |
| 74 | (structure) |
| 75 | (structure) |
| 76 | (structure) |

11. A pharmaceutical composition, comprising a compound according to claim 1 and a pharmaceutically acceptable carrier or excipient.

12. A method of treating or preventing an HBV infection in a subject in need thereof, comprising administering to the subject a therapeutically effective amount of a compound or a combination of compounds according to claim 1.

13. The method of claim 12, further comprising administering to the subject at least one additional therapeutic agent selected from the group consisting of HBV polymerase inhibitors, interferon, viral entry inhibitors, viral maturation inhibitors, capsid assembly or core protein inhibitors or modulators, reverse transcriptase inhibitors, TLR-agonists, inducers of cellular viral RNA sensor, therapeutic vaccines, RNA interence (RNAi) or small interfering RNA (siRNA) and combinations thereof.

14. The method of claim 13, wherein the compound and the at least one additional therapeutic agent are co-formulated.

15. The method of claim 13, wherein the compound and the at least one additional therapeutic agent are co-administered.

16. The method of claim 13, wherein administering the compound allows for administering of the at least one additional therapeutic agent at a lower dose or frequency as compared to the administering of the at least one additional therapeutic agent alone that is required to achieve similar results in prophylactically treating an HBV infection in an individual in need thereof.

17. The method of claim 13, wherein the subject is refractory to at least one compound selected from the group consisting of a HBV polymerase inhibitor, interferon, viral entry inhibitor, viral maturation inhibitor, distinct capsid assembly modulator, inducer of cellular viral RNA sensor, therapeutic vaccine, antiviral compounds of distinct or unknown mechanism, and combination thereof.

18. The method of claim 13, wherein the administering of the compound reduces viral load in the subject to a greater extent compared to the administering of at least one compound selected from the group consisting of a HBV polymerase inhibitor, interferon, viral entry inhibitor, viral maturation inhibitor, distinct capsid assembly modulator, inducer of cellular viral RNA sensor, therapeutic vaccine, antiviral compounds of distinct or unknown mechanism, and combination thereof.

19. The method of claim 13, wherein the method results in a lower incidence of viral mutation and/or viral resistance than administering a compound selected from the group consisting of a HBV polymerase inhibitor, interferon, viral entry inhibitor, viral maturation inhibitor, distinct capsid assembly modulator, inducer of cellular viral RNA sensor, therapeutic vaccine, antiviral compounds of distinct or unknown mechanism, and combination thereof.

* * * * *

UNITED STATES PATENT AND TRADEMARK OFFICE
CERTIFICATE OF CORRECTION

PATENT NO. : 10,729,688 B2  Page 1 of 2
APPLICATION NO. : 16/365742
DATED : August 4, 2020
INVENTOR(S) : Yao-Ling Qiu et al.

It is certified that error appears in the above-identified patent and that said Letters Patent is hereby corrected as shown below:

In the Claims

At Column 75
In Claim 5, Line 26 after -S(O)-, delete "S(O)-,".

At Column 76
In Claim 7, Line 21 after -S(O)-, delete "S(O)-,".

At Column 76 & Column 77
In Claim 9, Line 57 thru Lines 1-40 delete structures

"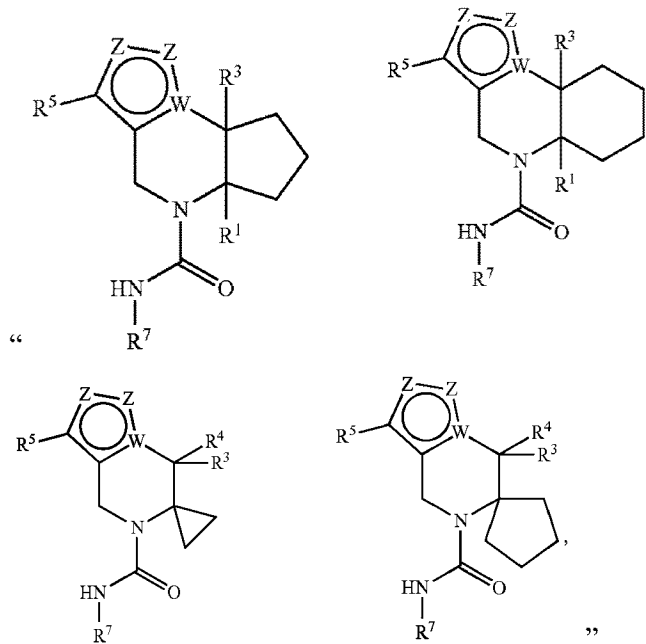,"

Signed and Sealed this
Sixth Day of October, 2020

Andrei Iancu
*Director of the United States Patent and Trademark Office* and insert -- 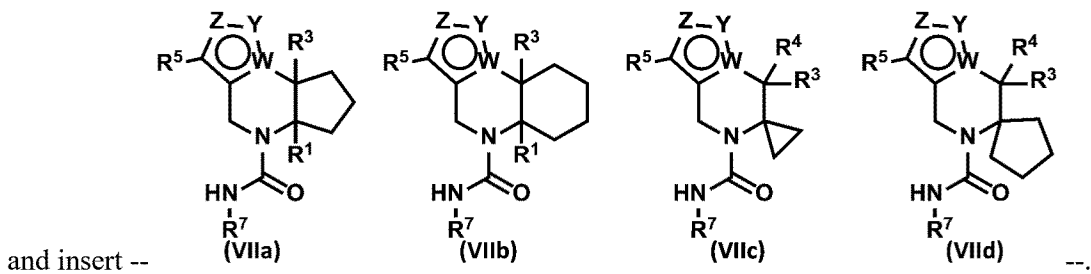 --.